US005512470A

United States Patent [19]

Sabesan

[11] Patent Number: 5,512,470

[45] Date of Patent: Apr. 30, 1996

[54] METHOD FOR INHIBITING SIALIDASE ACTIVITY

[75] Inventor: Subramaniam Sabesan, Wilmington, Del.

[73] Assignee: E. I. Du Pont de Nemours and Company, Wilmington, Del.

[21] Appl. No.: 444,593

[22] Filed: May 19, 1995

Related U.S. Application Data

[60] Division of Ser. No. 147,198, Nov. 3, 1993, Pat. No. 5,489,675, which is a continuation-in-part of Ser. No. 904, 233, Jun. 25, 1992, abandoned.

[51] Int. Cl.$^6$ .......... C12N 9/24

[52] U.S. Cl. .......... 435/200; 514/25; 514/53; 536/17.2; 536/53; 536/123.13

[58] Field of Search .......... 435/200; 514/25, 514/53; 536/17.2, 53, 123.13

[56] References Cited

U.S. PATENT DOCUMENTS

| | | | |
|---|---|---|---|
| 4,375,462 | 3/1983 | Berg et al. | 424/117 |
| 5,218,097 | 6/1993 | Ernst | 536/18.5 |
| 5,318,890 | 6/1994 | Rosen et al. | 435/7.24 |
| 5,330,897 | 7/1994 | Pindak et al. | 435/7.23 |
| 5,438,125 | 8/1995 | Okamoto et al. | 536/4.1 |

FOREIGN PATENT DOCUMENTS

| | | | |
|---|---|---|---|
| 3-262483 | 11/1991 | Japan | C12N 9/99 |

OTHER PUBLICATIONS

Burnet, F. M. et al, *Aust. J. Exp. Biol. Med. Sci.*, 25, 227–233 (1947).

Stone, J. D., *Aust. J. Exp. Biol. Med. Sci.*, 26, 48–64 (1948).

Pritchett, T. J. et al, *Virology*, 160(2), 502–506 (1987).

Pritchett, T. J. et al, *J. of Biological Chemistry*, 264(17), 9850–9858 (1989).

Air, G. M. et al, *J. of Virology*, 64(12), 5797–5803 (1990).

Nagai, T. et al, *Chem. Pharm. Bull.*, 38(5), 1329–1332 (1990).

Suzuki, Y. et al, *Glycoconjugate J*, 7, 349–356 (1990).

Sabesan, S., *Carbohydrate Research*, 218, 27–54 (1991).

Hasegawa, A. et al, *J. Carbohydrate Chem.*, 9(4), 369–392 (1990).

Sabesan, S. et al, *Canadian Journal of Chemistry*, 62(4), 644–654 (1984).

Sabesan, S. et al, *J. Am. Chem. Soc., 108(8), 2068–2080 (1986).*

Murase, T. et al, *Chemical Abstracts*, 112, Abstract No. 36327g (1990).

Weidmann, H. eta al, *Chemical Abstracts*, 86, Abstract No. 55643t, p. 461 (1977).

Jansson, K. et al, *J. Org. Chem.* , 53, 5629–5647 (1988).

Stout, E. I. et al, *J. Org. Chem.*, 40(9), 1331–1336 (1975).

Cox, J. M. et al, *J. Chem. Soc C*, 1121–1130 (1967).

Daniel, J. R. et al, *Carbohydrate Research*, 64, 69–79 (1978).

*Primary Examiner*—Douglas W. Robinson
*Assistant Examiner*—Kathleen Kahler Fonda

[57] ABSTRACT

Novel NeuAc-Gal dissacharide sialidase substrates and inhibitors which are locked into rigid conformation by the attachment of an alkyl group at the C-6 arm of the galactose core are provided. Also provided is a method for the inhibition of sialidase activity.

2 Claims, 11 Drawing Sheets

METHOD FOR INHIBITING SIALIDASE ACTIVITY

This is a division of U.S. application Ser. No. 08/147,198, filed Nov. 3, 1993, U.S. Pat. No. 5,489,675, issue date Feb. 6, 1996, which is a continuation-in-part of U.S. application Ser. No. 07/904,233, filed Jun. 25, 1992, now abandoned.

FIELD OF INVENTION

This invention provides novel disaccharide sialidase inhibitors and substrates and their intermediates. These compounds promise to function as powerful antiviral and anti-bacterial agents in cases where host-pathogen interaction is dependant on sialidase activity and hemagglutinin binding. The novel disaccharides are locked in a rigid conformation by the attachment of an alkyl group at the C-6 arm of the galactose which are analogues of both high and low energy forms of the compounds.

BACKGROUND OF THE INVENTION

Sialidases are enzymes present on viral protein coats and bacterial outer membranes. They serve to process the carbohydrate moieties of glycoproteins and glycolipids terminated with sialic acids that are found on host cell surfaces. The processing of these glycoprotein and glycolipid moieties are crucial in the pathogen replication cycle. A specific example of this particular host-pathogen species is the influenza virus and the erythrocyte. Influenza virus binds to the erythrocytes through attachment to cell surface carbohydrates. Specifically, the virus has a membrane envelope with two types of surface glycoproteins, the hemagglutinin and the neuraminidase (sialidase), both of which interact with sialyloligosaccharides on host (erythrocyte) cells. It has long been known that pretreatment of erythrocytes or host cells with bacterial sialidase abolishes viral adsorption and/or infection, demonstrating that sialic acid is an essential feature of the receptor determinant (Burnet, F. M. and Stone, J. D., Aust. J. Exp. Biol. Med. Sci., 25, 227–233 (1947) and Stone, J. D., Aust. J. Exp. Biol. Med. Sci., 26, 48–64 (1948)). Hemagglutinin attaches to the host cell structure which contains sialic acid, galactose and N-acetylglucosamine. Neuraminidase functions to hydrolyze the sialic acid from receptors, and at high pathogen levels in an infected cell this neuraminidase activity aids in elution of the budding virus from the host membrane, thus facilitating replication of the pathogen.

Given the mechanism of the influenza pathogenicity, two possible routes to inhibition of infection could be theorized. One route is the inhibition of viral hemagglutinin binding to the host cell, which would deny the virus its initial foothold on the cell surface. Several studies have attempted to design molecules that would competitively inhibit viral hemagglutinin binding. Pritchett et al., Virology, 160, 502–506 (1987), teach a procedure for evaluating the relative affinities of simple sialoside receptor determinants in their interaction with the receptor binding pocket of the influenza virus hemagglutinin. Pritchett determined that siaiosides with the NeuAcα2, 6Gal and NeuAcα2, 6GlcNAc linkages were 5–30 times more potent inhibitors than those with the NeuAcα2, 3Gal linkage.

Pritchett et al., J. Biol. Chem., 264, 9850–9859 (1989) teach that sialic acid and galactose are both important components of the natural substrate for initial viral recognition.

Sabesan et al. (U.S. Pat. No. 5,220,008) disclose heptasaccharides containing bivalent receptor trisaccharide determinants that bind the influenza virus with increased inhibitor potency. The compounds of Sabesan are two trisaccharide structures comprising sialic acid (N-acetylneuraminic acid), galactose and N-acetyl-glucosamine which are attached to another (anchoring) sugar molecule.

The second potential route to inhibition of viral infection involves the synthesis of compounds that serve as preferred binding substrates for the sialidase (typically neuraminidase) enzymes wherein these substrates could not be hydrolyzed, or would be hydrolyzed very poorly by the sialidase. Such substrates could function as competitive binding inhibitors. Attempts at inhibiting the active site of the sialidases have involved isolation of active components from bacterial cultures, plant extracts, or the production of enzyme site specific antibodies.

Frolov et al. (JP 0326248) report the isolation and partial characterization of an influenza neuraminidase inhibitor from *S. aurens* having a molecular weight of 94,0000–120,000 which demonstrated 100% inhibition of type A0, A1 or A2 influenza neuraminidase.

Air et al., J. Virol., 64, 5797–5803 (1990), describe monoclonal antibodies which inhibit influenza virus neuraminidase by binding to epitopes located on the rim of the enzyme active-site crater. Air evaluates neuraminidase inhibition by the monoclonal antibody NC41 from nineteen different influenza mutants and concludes that there is a high degree of strain specificity at the enzyme active site.

Nagai et al., Chem. Pharm. Bull., 38, 1329–1332 (1990), describe inhibition of influenza and mouse liver sialidases by flavonoids isolated from 103 species of plants. The inhibitory flavone compound was not fully characterized.

One of the difficulties in using the sialidase inhibitors described above as potential pharmaceuticals is that most remain generally uncharacterized and their specific mechanisms of action are unknown. Recently, carbohydrate moeities have been synthesized which have binding affinity for the sialidase active site but are not hydrolyzed. For example, Suzuki et al., Glycoconjugate, 7, 349–356 (1990), teach synthetic thioglycoside analogs of disaccharide gangliosides that competitively inhibit GM3 hydrolysis by the sialidase of different subtypes of human and animal influenza viruses.

In an effort to elucidate the three dimensional properties of possible sialidase substrates, Sabesan et al., Carbohydr. Res., 218, 27–54 (1991), examined the conformational characteristics of several synthetic sialyloligosaccharides present as terminal sequences in N and O-linked carbohydrate groups of glycoproteins. Sabesan teaches that for α-D-NeuAc-(2-6)-β-D-Gal linkages the C-6 arm of the galactose can potentially orient either in the low energy "gt" or the high energy "tg" orientation. In any given population the "gt" conformer will predominate over the "tg" conformer in ratios on the order of 85%:15%.

The present invention addresses two aspects of pathogen inhibition by providing novel disaccharide compounds that are expected to bind hemagglutinin (and thus function as competitive inhibitors with the natural substrate), but are either not hydrolyzed or are poorly hydrolyzed by sialidase. The invention also provides novel monosaccharide intermediates which are useful for preparation of these disaccharides. The novel (NeuAc-Gal) disaccharides are based on the natural trisaccharide substrate, αDNeuAc(2-6)βDGal(1-4)βDGlcNAc, which is present on glycoproteins and glycolipids found on host cell membranes. Applicant has discovered that with the addition of an alky group to the C-6 arm of the galactose (which prohibits free rotation about its C-6 to C-5 bond axis and freezes the structure in a rigid conformation) it is possible to create two conformer analogues of the disaccharides, a high energy and a low energy conformer, which differ in three dimensional conformation and which possess distinctly different properties. Applicant has found that only the high energy conformer is able to selectively bind or inhibit influenza virus sialidase activity. Neither the low energy conformer or the racemic mixtures of the instant compounds are effective enzyme inhibitors. Based on the general art and the work of Pritchett et al., J. Biol. Chem., 264, 9850–9859 (1989) and Sabesan et al., (U.S. Pat. No. 5,220,008) Applicant believes the instant compounds will serve as competitive inhibitors to pathogenic hemagglutinin binding to host cells. Further, Applicant has demonstrated that the freezing of the compounds in rigid conformation results in a dramatic change in sialidase substrate activity and thereby the instant compounds serve as useful inhibitors of the sialidase activity associated with pathogenic organisms.

SUMMARY OF THE INVENTION

This invention provides novel disaccharide compounds and their synthetic intermediates, comprising formulas I and II

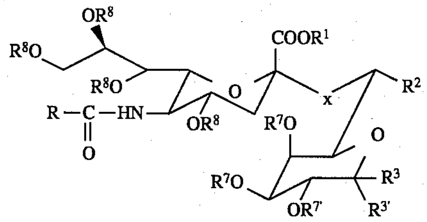

I

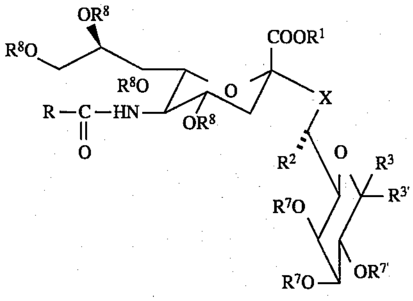

II wherein

R is H or a $C_1$ to $C_{20}$ hydrocarbyl or substituted hydrocarbyl;

$R^1$ is $C_1$ to $C_{20}$ alkyl, a mono, di or polyvalent cation of an alkali metal, alkaline earth metal or transition metal, or an ammonium or substituted ammonium ion;

X is O, S, $CR^4R^5$ or $NR^6$ wherein $R^4$, $R^5$ and $R^6$ may independently be H or a $C_1$ to $C_{20}$ hydrocarbyl or substituted hydrocarbyl;

$R^2$ is a $C_1$ to $C_{20}$ hydrocarbyl or substituted hydrocarbyl;

$R^3$ and $R^{3'}$ are H, OH, a $C_1$ to $C_{20}$ alkoxy or substituted alkoxy, a mono, di or oligosaccharide, or an alkylideneoxy taken together with $R^{7'}$ when $R^{7'}$ is not H; provided that one of $R^3$ or $R^{3'}$ must be H but $R^3$ and $R^{3'}$ may not both be H;

$R^7$ and $R^{7'}$ are H, acyl, or a $C_1$ to $C_{20}$ alkyl, aryl, or alkylidene taken together with an adjacent $R^3$, $R^{3'}$, $R^7$ or $R^{7'}$; and $R^8$ is H, acyl, or a $C_1$ to $C_{20}$ alkyl.

This invention also provides novel monosaccharide compounds comprising formula III and IV,

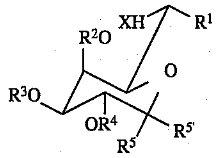

III

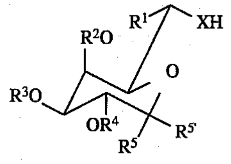

IV wherein $R^1$ is H or a $C_1$ to $C_{20}$ hydrocarbyl or substituted hydrocarbyl;

$R^2$ is H, a $C_1$ to $C_{20}$ alkyl, or an alkylidene taken together with $R^3$;

$R^3$ is H, a $C_1$ to $C_{20}$ alkyl, or an alkylidene taken together with $R^2$;

$R^4$ is H, a $C_1$ to $C_{20}$ alkyl, or an alkylidene taken together with $R^5$ when $R^5$ is alkoxy;

$R^5$ is H, a $C_1$ to $C_{20}$ alkoxy, or an alkylideneoxy taken together with $R^4$;

$R^{5'}$ is H, a $C_1$ to $C_{20}$ alkoxy, or a mono, di or oligosaccharide; provided that one of $R^5$ or $R^{5'}$ must be H and $R^5$ and $R^{5'}$ may not both be H;

X is O, S, $CR^6R^7$ or $NR^8$, wherein $R^6$, $R^7$ and $R^8$ are independently H or a $C_1$ to $C_{20}$ hydrocarbyl or substituted hydrocarbyl.

The invention further provides a method for inhibiting sialidase activity comprising contacting a sialidase enzyme with the high energy disaccharide conformer compound of Formula I above, wherein X is S.

DETAILED DESCRIPTION OF THE INVENTION

Figure 1A:
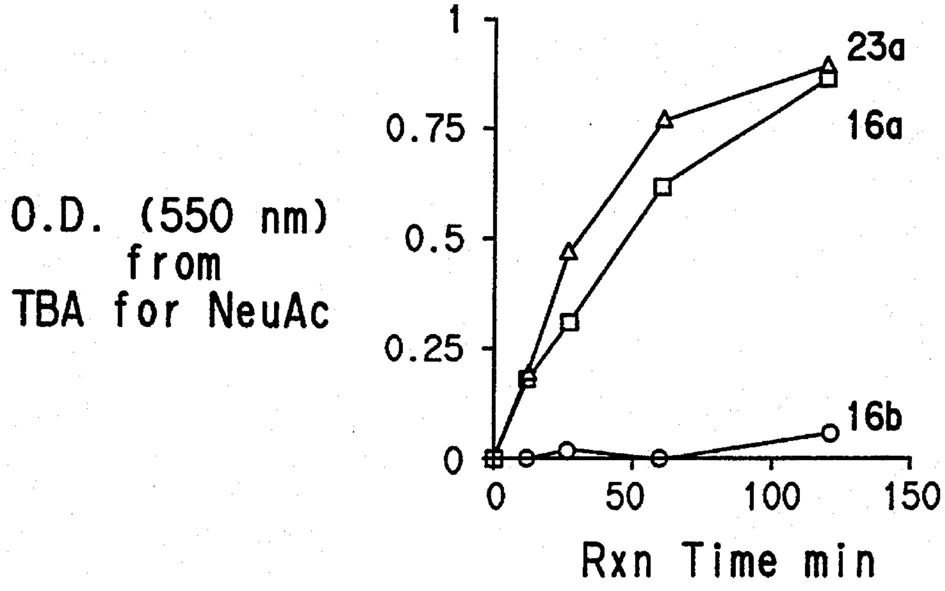
FIG. 1 illustrates a time course of hydrolysis of sialoside compounds 23a, 16a and 16b by neuraminidases from *A. ureafaciens* (FIG. 1A), *C. perfringens* (FIG. 1B), *V. cholerae* (FIG. 1C) and influenza virus neuraminidase (FIG. 1D).
Figure 1B:
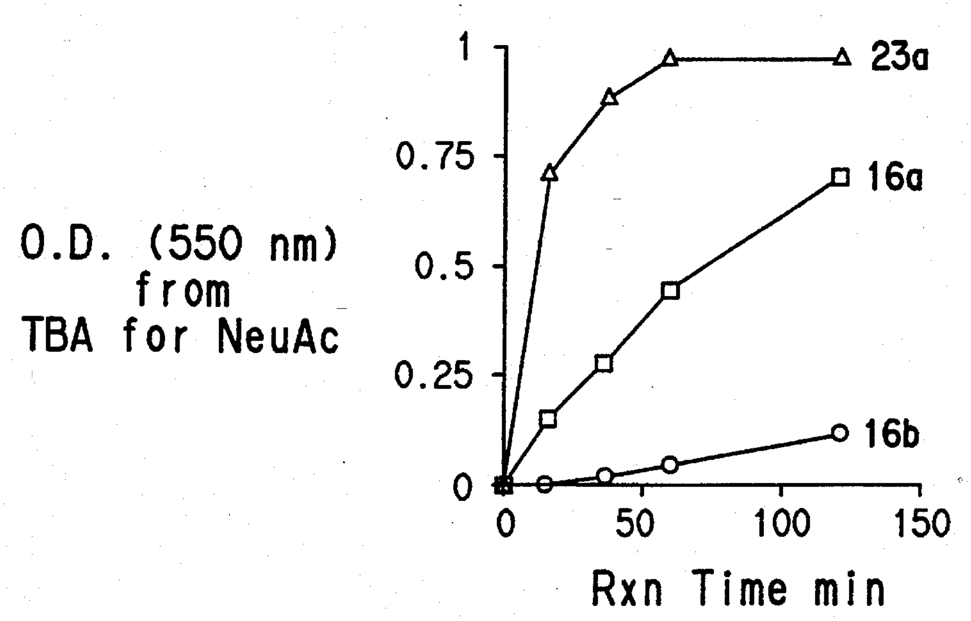
Figure 1C:
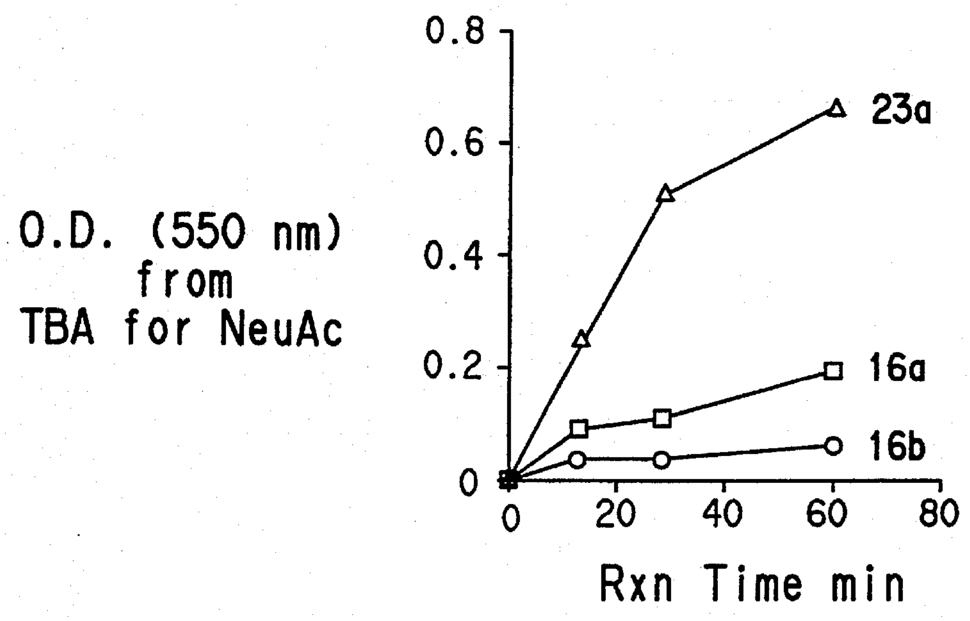
Figure 1D:
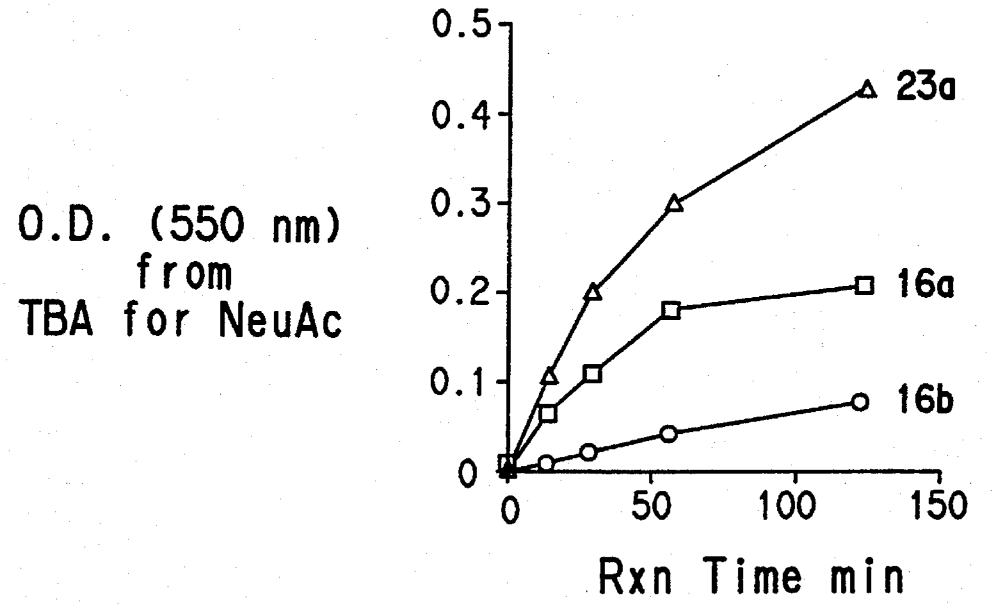
Figure 2A:
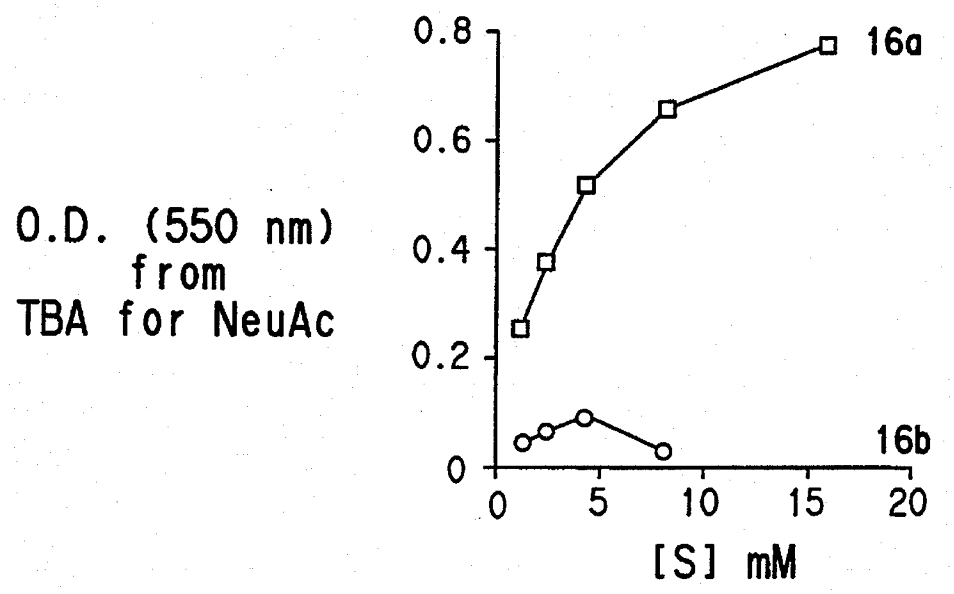
FIG. 2 illustrates hydrolysis of sialoside analogs 16a and 16b at various concentrations by neuraminidases from influenza A (FIG. 2A), *A. ureafaciens* (FIG. 2B), *C. perfringens* (FIG. 2C), and *V. cholerae* (FIG. 2D).
Figure 2B:
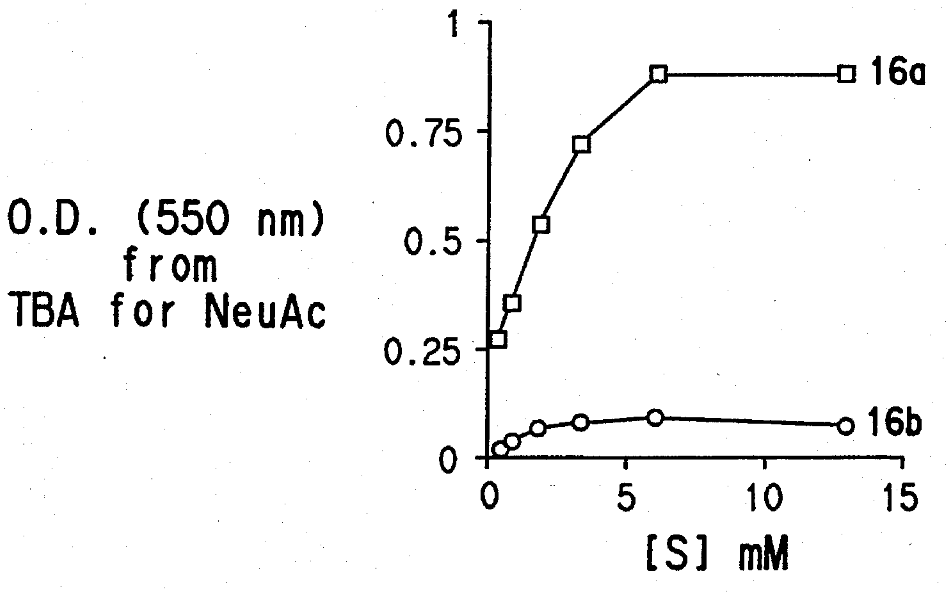
Figure 2C:
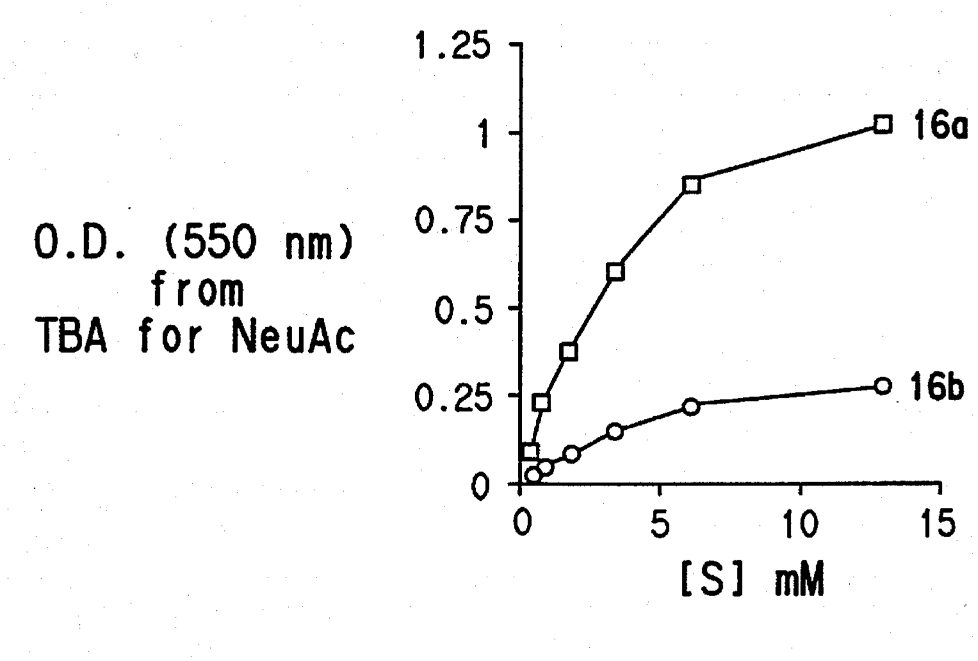
Figure 2D:
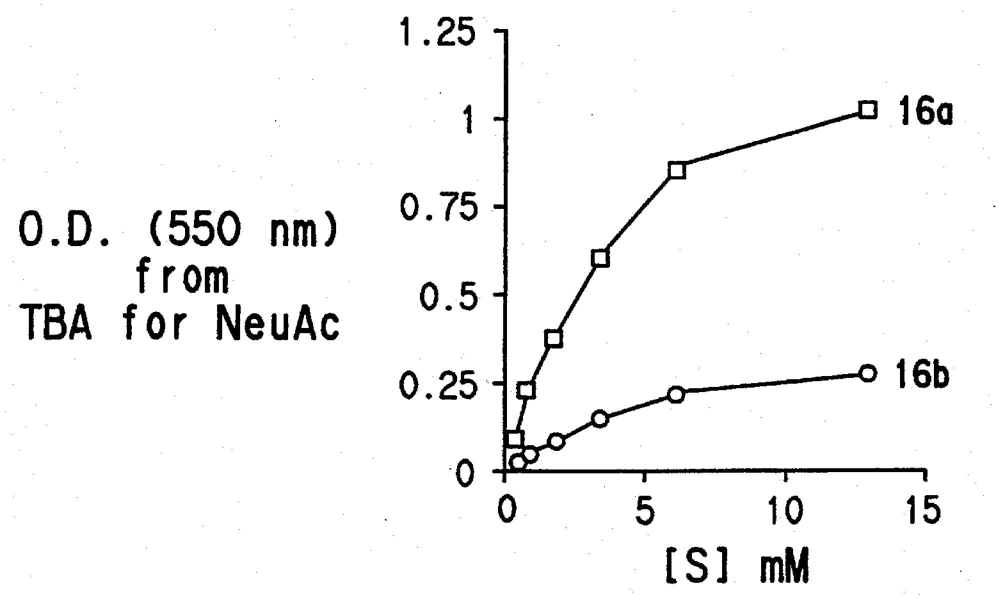
Figure 3A:
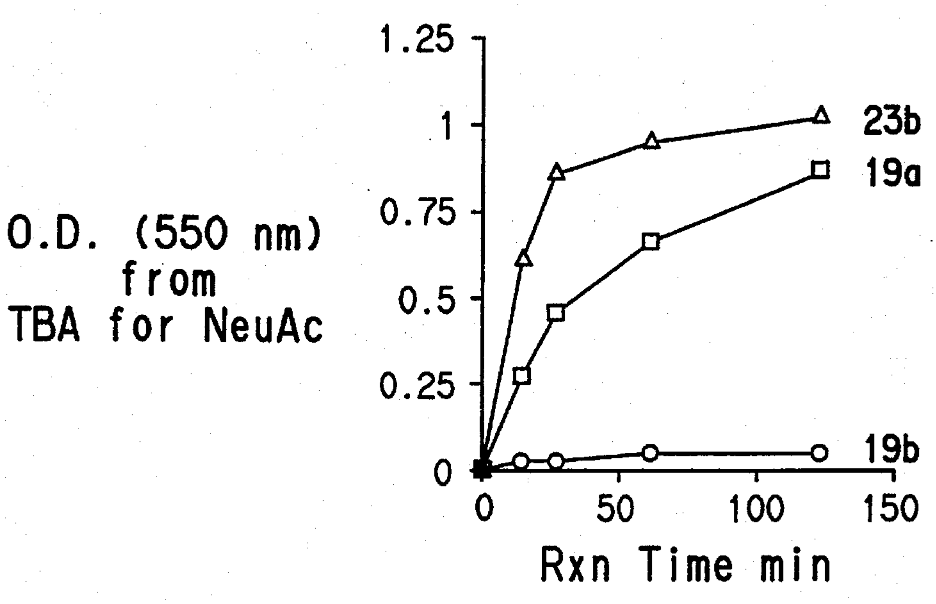
FIG. 3 illustrates the time course of hydrolysis of the isopropylidenated sialosides 23b, 19a and 19b by neuraminidases from *A. ureafaciens* (FIG. 3A), *C. perfringens* (FIG. 3B) , and *V. cholerae* (FIG. 3C) and influenza virus neuraminidase (FIG. 3D).
Figure 3B:
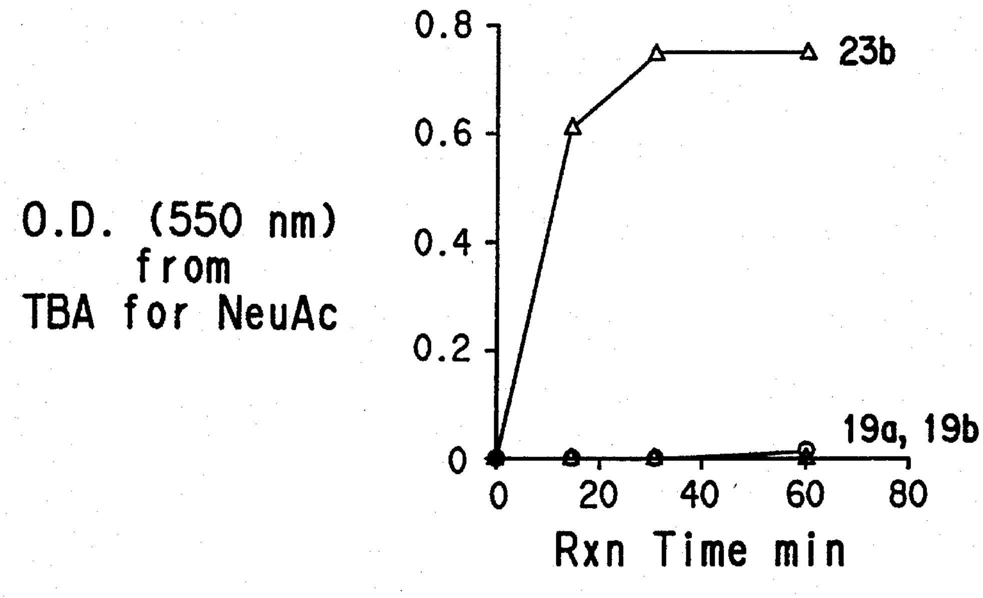
Figure 3C:
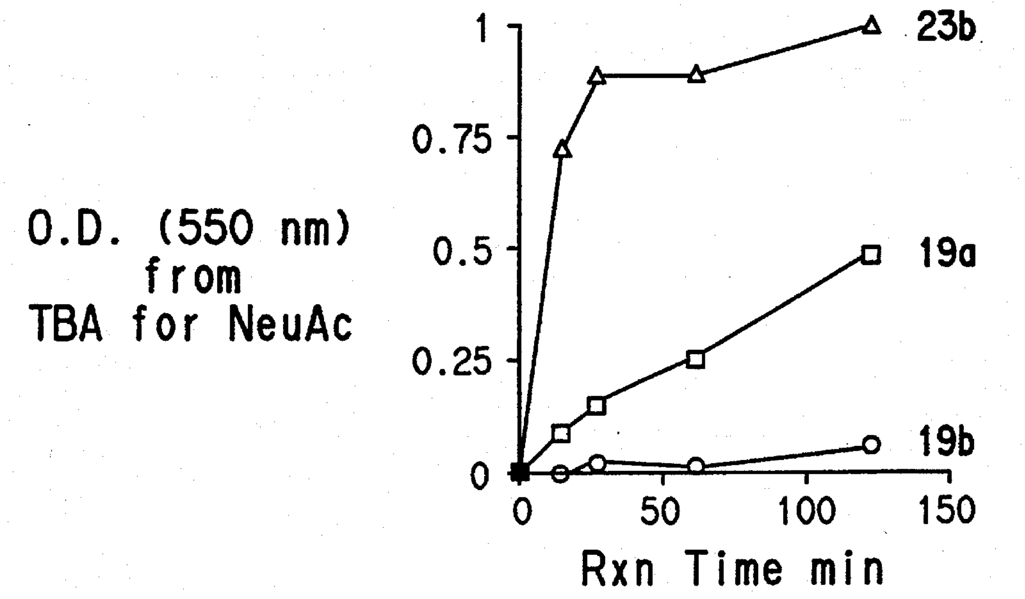
Figure 3D:
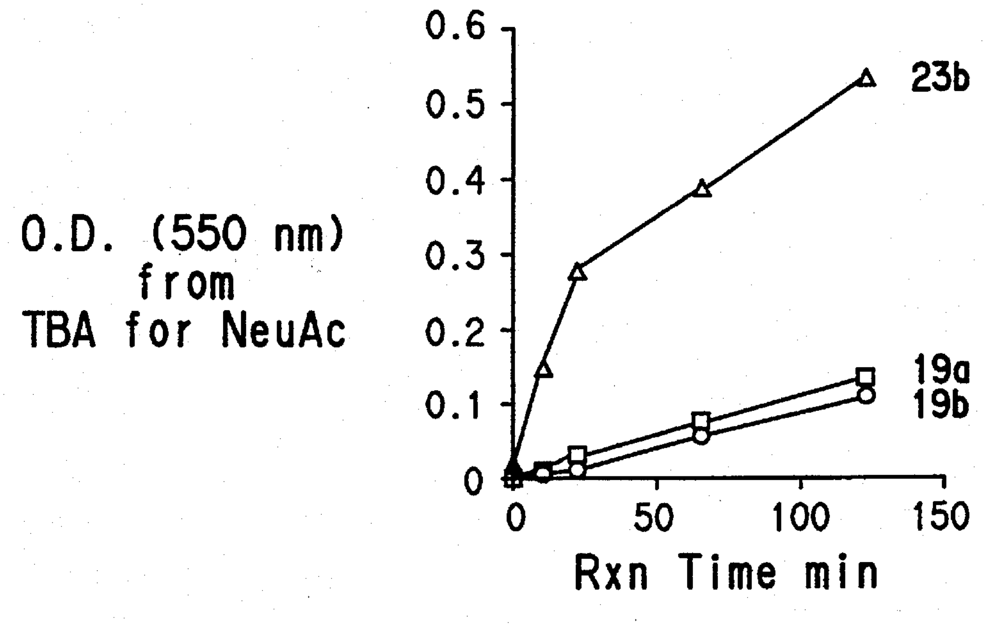

The present invention relates to novel disaccharide sialidase substrates which have been stabilized in rigid conformations by the attachment of an alkyl group at the C-6 arm of the galactose.

The novel disaccharide compounds are analogs of the high and low energy disaccharide conformers exemplified by compounds 16a & 16b, shown below, and structures exemplified by compounds 22a & 22b which represent the sulfur analogs of 16a & 16b.

Unexpectedly, it is seen that the disaccharides attaining a low energy conformation (e.g., 16b), which most resemble the natural disaccharide substrate, are in fact, poor sialidase substrates having a lower binding affinity and Vmax for sialidase than the corresponding high energy forms. Conversely, the high energy form of the disaccharides (e.g., 16a) demonstrate a binding affinity comparable with the natural disaccharide substrate. Similarly, it is seen that the high energy sulfur analog of 16a (22a) exhibits high binding affinity for the sialidase reactive site and is a far superior inhibitor of enzyme activity compared with the sulfur analog of the low energy conformer 16b (22b). Thus, it is the uncommon, high energy form of the molecule that is the preferred binding substrate. Sulfur analogs of the high and low energy disaccharide substrates (e.g., 22a and 22b) cannot be hydrolyzed by sialidase. In spite of their different binding affinities and susceptibility to sialidase, all four forms of the dissaccharides are expected to retain their ability to bind hemagglutinin.

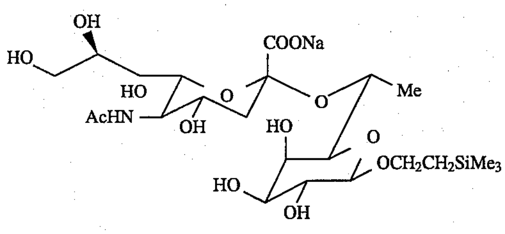
16a

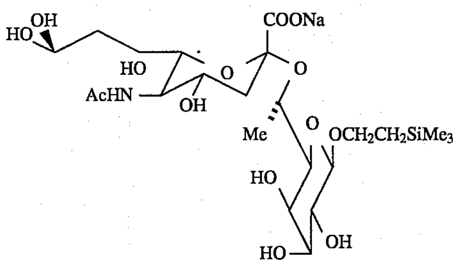
16b

-continued

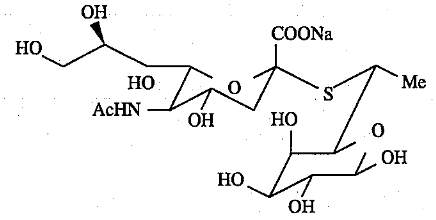
22a

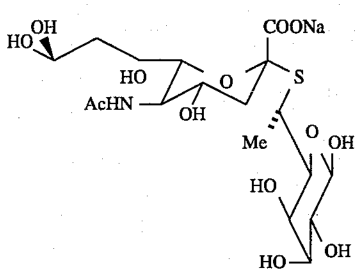
22b

The disaccharides represented below (23a) are different conformers of the same compound which comprise two sugar moieties; sialic acid and galactose. The compounds typically exist in solution as an equilibrium mixture with an overwhelming preference in favor of the low energy conformer (greater than 85%, Sabesan et al., Carbohydr. Res., 218, 27–54 (1991)).

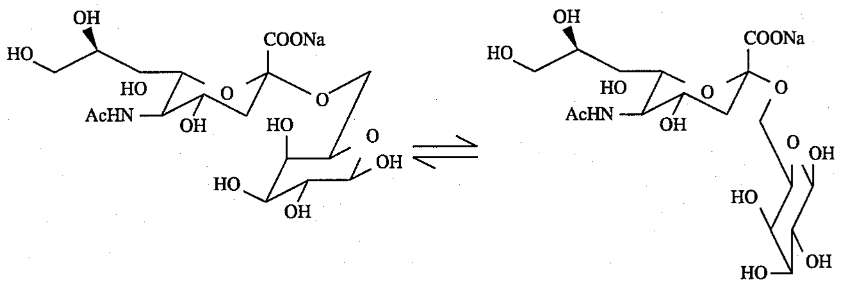
23a

High Energy

Low Energy

In order to maximize substrate binding and determine which conformer has the highest affinity for the sialidase active site, it is necessary to somehow prepare rigid compounds resembling the high or low energy conformations of 23a. This has been accomplished by attaching an alkyl group at the C-6 arm of the galactose of compound 23a to produce the corresponding high and low energy forms exemplified by 16a and 16b (above). Any alkyl group will produce this effect, however $CH_3$ is most preferred.

Interestingly, the sulfur analog of the parent substrate compound 23a (shown as 23c below) proved to be a poor sialidase inhibitor.

$R^8$ is H, acyl, or a $C_1$ to $C_{20}$ alkyl.

The following definitions and abbreviations will be used for claim interpretation and in structure schemes 1–3 for the purposes of this disclosure.

"Ac" is acetyl

"Bn" is benzyl

"Protected sugar" refers to when the OH groups of the monosaccharide, disaccharide or polysaccharide are functionalized.

"Hydrocarbyl" refers to any alkyl, alkenyl or alkynyl group, straight chained, branched or cyclic which is comprised of CH(n) moieties wherein n is 0 to 3.

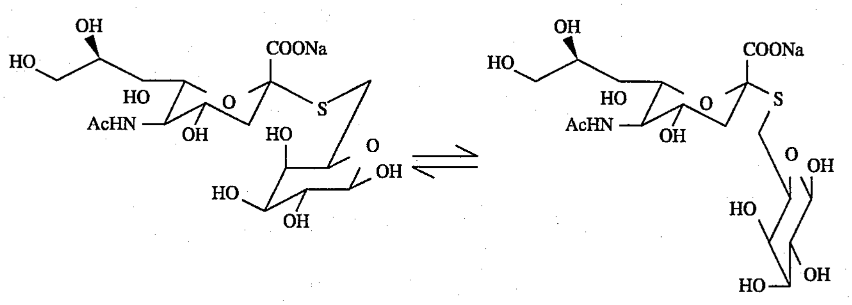

23c

High Energy

Low Energy

The disaccharides of the present invention comprise the general formula I and II

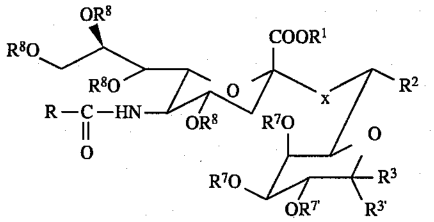

I

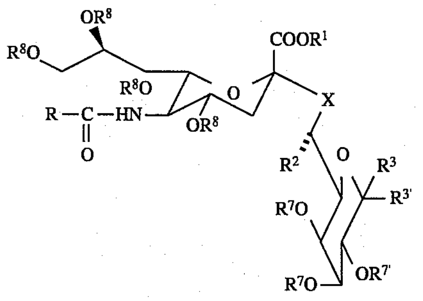

II wherein

R is H or a Cl to $C_{20}$ hydrocarbyl or substituted hydrocarbyl;

$R^1$ is a $C_1$ to $C_{20}$ alkyl, a mono, di or polyvalent cation of an alkali metal, alkaline earth metal or transition metal, or an ammonium or substituted ammonium ion;

X is O, S, $CR^4R^5$, or $NR^6$ wherein $R^4$, $R^5$, and $R^6$ are independently H or a $C_1$ to $C_{20}$ hydrocarbyl or substituted hydrocarbyl;

$R^2$ is a $C_1$ to $C_{20}$ hydrocarbyl or substituted hydrocarbyl;

$R^3$ and $R^{3'}$ are independently H, OH, a mono, di or oligosaccharide, a $C_1$ to $C_{20}$ alkoxy or substituted alkoxy, or an alkylideneoxy taken together with $R^{7'}$ when $R^{7'}$ is not H; provided that one of $R^3$ or $R^{3'}$ must be H but both $R^3$ and $R^{3'}$ may not be H;

$R^7$ and $R^{7'}$ are independently H, acyl, a $C_1$ to $C_{20}$ alkyl, aryl, or alkylidene taken together with an adjacent $R^3$, $R^{3'}$, $R^7$ or $R^{7'}$; and By "substituted ammonium ion", Applicant means NRRRR, wherein each R is independently H, or a $C_1$ to $C_{20}$ hydrocarbyl or substituted hydrocarbyl.

By "substituted alkoxy" Applicant includes alkoxy substituted, for example, with trimethylsilyl and halogen groups.

"Substituted hydrocarbyl" refers to a hydrocarbyl which has been substituted by at least one of the following groups: halogen, ether, oxo, ester, carboxy, amine, amide, sulfide, sulfoxide, sulfone or aryl.

"Aryl" refers to phenyl or naphthyl substituted with 0 to 3 of the following groups: alkyl, halogen, ether, oxo, ester, carboxy, amine, amide, sulfide, sulfoxide or sulfone.

"Sialidase" (neuraminidase) is an enzyme capable of hydrolyzing sialic acid (n-acetylneuraminic acid) which is α-linked to an oligosaccharide.

STRUCTURE SCHEME 1

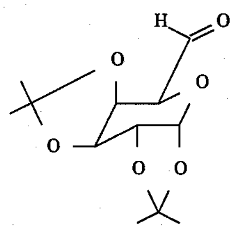

1

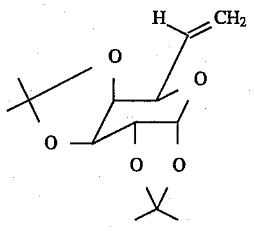

4c

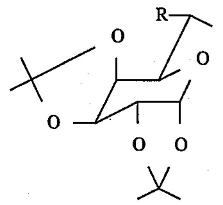

2a R = OH

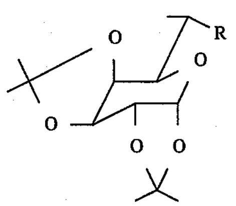

2b

-continued

STRUCTURE SCHEME 1

| | | |
|---|---|---|
| 3a | $R = OCH_2CH{=}CH_3$ | 3b |
| 3c | $R = OAc$ | 3d |
| 4a | $R = SCOCH_3$ | 4b |
| 5a | $R = SH$ | 5b |

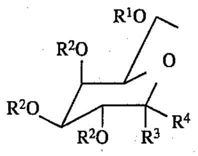

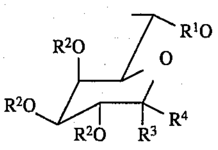

-continued

STRUCTURE SCHEME 1

| | | |
|---|---|---|
| 6a | $R^1$ = allyl, $R^2$ = OAC, $R^3$ = OAc and $R^4$ = H or $R^3$ = H and $R^4$ = OAc | 6b |
| 7a | $R^1$ = allyl, $R^2$ = OAc, $R^3$ = Br, $R^4$ = H | 7b |
| 8a | $R^1$ = allyl, $R^2$ = OAc, $R^3$ = H, $R^4 = O(CH_2)_2SiMe_3$ | 8b |
| 9a | $R^1$ = allyl, $R^2 = R^3$ = H, $R^4 = O(CH_2)_2SiMe_3$ | 9b |
| 10a | $R^1$ = allyl, $R^2$ = OBn, $R^3$ = H, $R^4 = O(CH_2)_2SiMe_3$ | 10b |
| 11a | $R^1 = R^3$ = H, $R^2$ = OBn, $R^4 = O(CH_2)_2SiMe_3$ | 11b |

STRUCTURE SCHEME 2

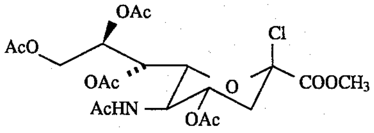

12a

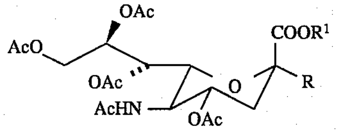

12b, R = SMe
12c, R = SCSOEt

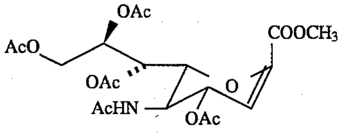

13

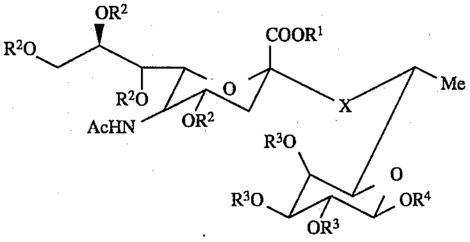

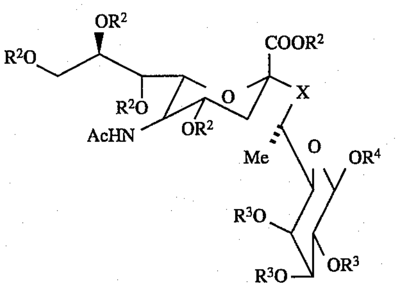

| | | | |
|---|---|---|---|
| 14a, | X = O, $R^1$ = Me, $R^2$ = OAc, $R^3$ = Bn, $R^4 = (CH_2)_2SiMe_3$ | 14b, | X = O, $R^1$ = Me, $R^2$ = OAc, $R^3$ = Bn, $R^4 = (CH_2)_2SiMe_3$ |
| 15a, | X = O, $R^1$ = Me, $R^2 = R^3$ = H, $R^4 = (CH_2)_2SiMe_3$ | 15b, | X = O, $R^1$ = Me, $R^2 = R^3$ = H, $R^4 = (CH_2)_2SiMe_3$ |
| 16a, | X = O, $R^1$ = Na, $R^2 = R^3$ = H, $R^4 = (CH_2)_2SiMe_3$ | 16b, | X = O, $R^1$ = Na, $R^2 = R^3$ = H, $R^4 = (CH_2)_2SiMe_3$ |
| 16c, | X = O, $R^1$ = Na, $R^2 = R^3$ = H, $R^4$ = H | 16d, | X = O, $R^1$ = Na, $R^2 = R^3$ = H, $R^4$ = Me |
| 22a, | X = S, $R^1$ = Na, $R^2 = R^3 = R^4$ = H | 22b, | X = S, $R^1$ = Na, $R^2 = R^3 = R^4$ = H |

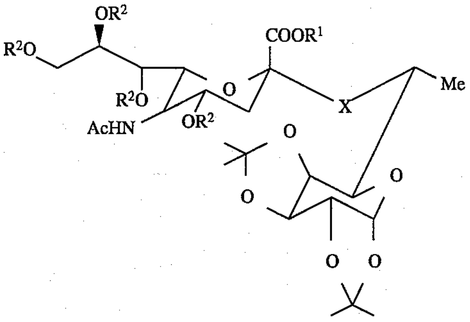

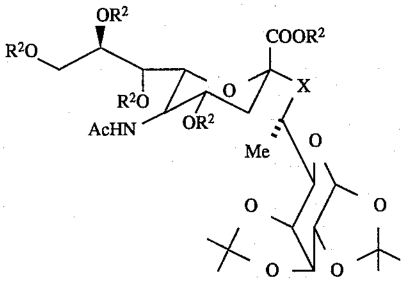

-continued
STRUCTURE SCHEME 2

| | |
|---|---|
| 17a, $X = O, R^1 = Me, R^2 = OAC$ | 17b |
| 18a, $X = O, R^1 = Me, R^2 = H$ | 18b |
| 19a, $X = O, R^1 = Na, R^2 = H$ | 19b |
| 20a, $X = S, R^1 = Me, R^2 = OAc$ | 20b |
| 21a, $X = S, R^1 = Me, R^2 = H$ | 21b |

STRUCTURE SCHEME 3

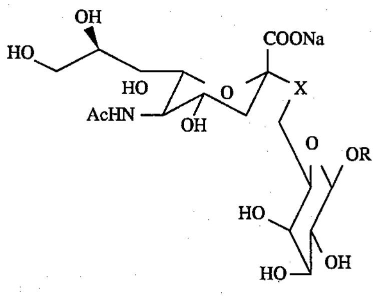

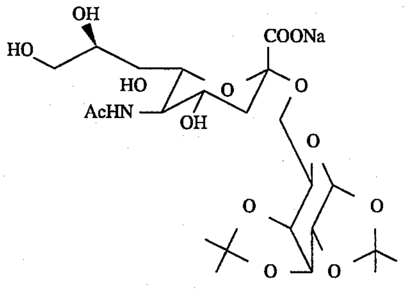

23a, $X = O, R = -CH_2CH_2SiMe_3$ 23b

23c, $X = S, R = H$

25, $X = O, R = DGlcNAc$

Preparation and purification of the compounds of Schemes 1–3 were preformed using techniques and materials readily available and well known to those skilled in the art.

Synthesis of O-Sialoside Analogs

The list of intermediates involved in the preparation of sialosides 16a, 16b, 19a, and 19b are indicated in Scheme 1. These intermediates may be prepared starting with 1,2;3,4-di-O-isopropylidene-1,6-dialdohexopyranose (1) as taught in Arrick, R. E. et al., *Carbohydr. Res.* 1973, 26, 441–447. Reaction of 1 with methyl magnesium iodide gave a 1:3 mixture of 2a and 2b. The stereoselectivity of 2a to 2b was about 1:1 with methyl magnesium bromide and 2.5:1 with methyl magnesium chloride. These two alcohols, which had identical mobility on silica gel, were separated after derivatization to their O-allyl ethers 3a and 3b or O-acetates 3c and 3d. To establish structural identity, the pure O-acetylated products were de O-acetylated to get authentic samples of 2a and 2b and compared to literature data (Lemieux, R. U.; Wong, T. C.; Thogersen, H. *Can. J. Chem.* 1981, 60, 81–86).

Specifically, the mixture of 2a and 2b was converted to the bromide 7a and 7b via O-allylation with allyl bromide-NaH followed by the separation of the two diastereomers to give 3a and 3b, de-O-isopropylidenation with 90% aqueous trifluoroacetic acid, acetylation with acetic anhydride-pyridine to give 6a and 6b, followed by the selective removal of the anomeric acetates with hydrazinc-acetate as taught by Excoffier, G. et al., (*Carbohydr. Res.* 1975, 39, 368–373) and then reacted with Viismeier bromide as further taught by Hepburn, D. R. et al., (*J. Chem. Soc. Perkin Trans. I* 1976, 754–757). The bromides 7a and 7b were then reacted with 2-(trimethylsilyl)ethanol in the presence of silver triflate-collidine complex to give the β-glycosides 8a and 8b.

The conversion of 8a and 8b to 11a and 11b was achieved under well-established conditions, namely de-O-acetylation followed by alkylation with benzyl bromide and sodium hydride to give 10a and 10b. Removal of the O-allyl group with iridium reagent afforded the alcohol 11a and 11b. Use of iridium in this fashion is well known in the art, for example see Oltvoort, J. J. et al., *Synthesis* 1981, 305–308.

The sialosides 14a or 14b, were prepared by glycosylation of 11a and 11b with the thioglycoside 12b. The thioglycoside glycosyl donor 12b was prepared in one step from the chlorosugar (12a) by reaction with sodium thiomethylate in acetonitrile. The yield was over 86%. Due to satisfactory purity of the crude product (>90%, the remainder of material was the glycal 13), chromatographic purification was not required at this point. This one step procedure for α-thiosialoside is superior in terms of purity and yield, as compared to the multi-step literature method as taught by Hasegawa, A. et al., *J. Carbohydr. Chem.* 1986, 5, 11–19.

The condensation of the alcohol 11a or 11b with thioglycoside 12b in the presence of methylsulfenyl triflate gave greater than 60% yield of the desired α-sialosides 14a or 14b. The minor β-sialoside was separated by chromatography. The structures of the α-sialosides 14a and 14b as well as the β-sialosides were established by NMR by identifying the chemical shifts of H-4 of NeuAc unit (4.80 ppm for α-sialoside and 5.3 ppm for β-sialoside).

The benzyl and the O-acetate protecting groups were removed by hydrogenation and subsequent treatment with sodium methoxide to yield the methyl ester of the sialosides (15a and 15b). These methyl esters were converted to the sodium salts 16a and 16b, respectively by treatment with Chelex-resin (sodium form).

The two di-O-isopropylidene sialosides 19a and 19b were synthesized via the protected sialosides 17a and 17b, which in turn were prepared by the condensation of alcohol 2a and 2b with the thioglycoside 12b or 12c under the conditions described for 14a. The methyl esters in 18a and 18b were hydrolyzed to the sodium salts 19a and 19b by treatment with Chelex resin as described above. Finally, the reducing sugar 16c was prepared from 19a by the removal of the isopropylidene groups with aqueous trifluoroacetic acid.

The natural sialoside derivative αDNeuAc (2-6) βDGal-$OCH_2CH_2Si(CH_3)_3$ (23a) was prepared by reacting (2-trimethysilyl)-ethyl 3-O-benzoyl-β-D-galactopyranoside (as prepared by Hasegawa, A. et al., *J. Carbohydr. Chem.* 1986, 5, 21–31) with 12b according to the procedure described for 14a followed by the removal of the protecting groups. Comparison of NMR data with the literature report (Murase, T. et al., *J. Carbohydr. Chem.* 1989, 8, 265–283) confirmed its structure. Similarly, the sialoside 23b was prepared by reacting 1,2; 3, 4-di-O-isopropylidene-α-D-galactopyranose with 12b followed by removal of the protecting groups.

Synthesis of S-Sialoside Analogs

To prepare the thiosialoside analogs 22a and 22b, the sodium thiolate derivatives of 5a and 5b were required for condensation with the chlorosugar 12a. These were prepared from 2a and 2b by converting them to their 6-O-trifluoromethanesulfonates (triflates) followed by displacement with potassium thioacetate. The desired product 4b (46% from 2a) was obtained together with an equal amount of the eliminated product 4c (about 49%). In contrast, the formation of 4a from the 6-O-triflate of 2b was more facile and the product 4a was obtained from 2b in 83% yield. The S-acetyl groups from 4a and 4b were removed by treatment with ammonium hydroxide in the presence of 1,4-dithiothreitol to give 5a and 5b. Condensation of the sodium salt of 5a or 5b with the chlorosugar 12a gave the thiosialosides 20a or 20b in greater than 60% yield. The products were contaminated with about 10% of the glycal 13 (compounds 20a, 20b and 13 exhibited identical mobility on silica gel). This latter impurity was removed by gel permeation chromatography of the de-O-acetylated derivatives 21a and 21b. Analytical samples of 20a and 20b were prepared by O-acetylation of pure 21a and 21b. The isopropylidene groups in 21a and 21b were removed by treatment with 50% aqueous trifluoroacetic acid and the methyl ester was hydrolyzed with Chelex resin to give 22a and 22b.

The thiosialoside 23c was prepared similarly from 1,2;3,4-di-O-isopropylidene-α-D-galactopyranose via the sodium salt of 6-deoxy-1,2;3,4-di-O-isopropylidene-6-thio-α-D-galactopyranose, which was then reacted with 12a as described above for 22a or 22b.

Synthesis of 14C- labeled Sialosides $^{14}$C-Labeled αDNeuAc (2-6) βDGal (1-4) βDGlcNAc (25) was needed for evaluation of the inhibitory potencies of the thiosialosides. It was prepared enzymatically from $^{14}$C-N-acetyllactosamine using Galβ1,4GlcNAcα2, 6 sialyltransferase according to a published procedure (Unversagt, C.; et al., *J. Am. Chem. Soc.* 1990, 112, 9308–9309.; Sabesan, S. et al., *J. Am. Chem. Soc.* 1986, 108, 2068–2080). The $^{14}$C-labeled N-acetyllactosamine was made enzymatically from the commercially available $^{14}$C-GlcNAc, using a modification of a methods well known in the art (Unversagt, C.; et al., *J. Am. Chem. Soc.* 1990, 112, 9308–9309; Rosevear, P. R. et al., *Biochemistry* 1982, 21, 1421).

Neuraminidase Assays

The relative rates of hydrolysis of the instant oxygen analogues were determined by measuring the activity of the neuraminidase enzyme using a colorimetric method essentially as described by Montreuil, J. et al., in *Glycoproteins;* Chaplin, M. F. Kennedy, J. F.; IRL Press, Washington, DC., 1986; pp 190–193. The neuraminidases tested included *Arthrobacter ureafaciens neuraminidase* (EC 3.2.1.18, specific activity 81.6/mg), *Clostridium perfringens neuraminidase* (EC 3.2.1.18) and *Vibrio cholerae neuraminidase* (EC 3.2.1.18) all purchased from Calbiochem® (La Jolla, Calif.) as well as Influenza A virus (WSN H1N1) whole virus suspension containing vital neuraminidase. Briefly, samples containing substrate and enzyme are diluted with deionized water, followed by the addition of 0.2 M sodium periodate in 9 M phosphoric acid solution. After 20 min at room temperature, the excess periodate was destroyed with 10% sodium arsenite in 0.5 M sodium sulfate-0.1 N sulfuric acid solution followed by the addition of 0.6% thiobarbituric acid in 0.5 M sodium sulfate solution. Samples are cooled to room temperature, the color extracted with cyclohexanone (2 mL), and the optical density measured at 550 nm.

Inhibition of Neuraminidases by Thiosialosides

In order to determine the effectiveness of the instant thiosialosides as neuraminidase inhibitors, incubations were preformed involving the neuraminidase, the thiosialoside inhibitor and a $^{14}$C-labled substrate, $^{14}$C-Labeled αDNeuAc (2-6) βDGal (1-4) βDGlcNAc (25) described above. Inhibition constants of the inhibitors were determined by incubating (37° C.) a solution of 25 at four different concentrations with the neuraminidase, in the presence or absence of the inhibitors. After the reaction, the reaction mixture was diluted with deionized water and passed through a column of Dowex resin. The column was further eluted with deionized water. Under these conditions, only the free LacNAc elutes. The eluant was diluted with Scintillation fluid (10 mL, Formula 989, NEN, MA) and the radioactivity was measured, and the amount of free LacNAc liberated was determined.

EXAMPLES

GENERAL METHODS

Unless otherwise specified all the reagents were purchased from Aldrich Chemical Co (St. Louis, Mo.). Thin layer chromatography was performed on precoated plates of Silica Gel 60 $F_{254}$ (EM Science), and the spots were visualized with a spray containing 5% sulfuric acid in ethanol, followed by heating. Column chromatography was done on silica gel 60 (230–400 mesh, EM Science). $^{1}$H NMR spectra were recorded at 300, 500 or 600 MHz (GE Omega-300, GE Omega 500 or Bruker AM-500, AMX-600) and the $^{13}$C- NMR spectra were recorded with the above instruments operating at 75.48 or 125.74 MHz (300 and 500 MHz, respectively for proton). The hydrogen and carbon chemical shifts in organic solvents are expressed relative to tetramethylsilane (TMS). The hydrogen and carbon atoms are numbered from the reducing end units. Thus, the galactose unit atoms in 16a or 16b are denoted by 1 to 7 and the NeuAc unit atoms are denoted by 1' to 9'. For solutions of compounds in deuterium oxide or deuterated methanol, the hydrogen chemical shift values are expressed relative to the HOD signal (4.75 ppm at 296° K. internal acetone 2.23 ppm), and the carbon chemical shifts are expressed relative to external TMS using the deuterium lock of the spectrometer, which set the chemical shifts of 1,4-dioxane at 66.9 ppm.

EXAMPLE 1

Synthesis of 6-O-Allyl-7-deoxy-1,2:3,4-di-O-isopropylidene-a-D-glycero-D-galactoheptopyranose (3a) and 6-O-allyl-7-deoxy,1,2: 3,4-di-O-isopropylidene-β-L-glycero-D-galactoheptopyranose (3b)

1, 2; 3, 4-Di-O-isopropylidene-1,6-dialdohexopyranose (71.5 g) was prepared by standards (Arrick, R. E. et al. *Carbohydr. Res.* 1973, 26, 441–447) and reacted with methyl magnesium iodide according to Lemieux et al. (*Can. J. Chem.* 1981, 60, 81–86) to get a syrup (71.6 g) . The product was dissolved in anhydrous dimethylformamide (DMF, 800 ml) . Sodium hydride ( 6.3 g) followed by allyl bromide (23 ml) were added and the reaction mixture was stirred at room temperature for 24 h. Another portion of sodium hydride (3.5 g) and allyl bromide (10 ml) were added and the reaction was continued for 3 more days. The reaction mixture was quenched with methanol (5 ml) and the solvents were evaporated. The residue was dissolved in dichloromethane and washed with water, ice cold hydrochloric acid, and saturated sodium bicarbonate solution. The solvent was evaporated and the two major products were separated by chromatography on a column of silica gel using ethyl acetate—hexane (1:15 in the beginning and 3:8 at the end) as column eluant. The less polar component was identified as 6-O-allyl-7-deoxy- 1 2;3,4-di-O-isopropylidene-α-D-glycero-D-galactoheptopyranose (3a, tlc, ethyl acetate-hexane=3:8; $R_f$=0.56, 15.2 g), whereas the more polar product ($R_f$=0.50) was established as 6-O-allyl-7-deoxy-1,2;3,4-di-O-isopropylidene-β -L-glycero-D-galacto-heptopyranose (3b) (28.1 g).

3a, $[\alpha]_D^{25}$–40±2° C. (c 1.0, $CHCl_3$). $^1$H NMR ($CDCl_3$) δ: 5.94 (m, —CH=C), 5.51 (d, J=4.9 Hz, H-1), 5.31–5.11 (m, $CH_2$=C), 4.57 (dd, J=2.4, 8.2 Hz, H-3), 4.45 (dd, J=1.8, 8.2 Hz, H-4), 4.26 (dd, J=2.4, 4.9 Hz, H-2), 4.15–3.99 (m, O—$CH_2$—C=), 3.64 (d×quartet, J=6.1, 9.2 Hz, H-6), 3.53 (dd, J=1.5, 9.2 Hz, H-5), 1.51, 1.44, 1.34 and 1.31 (isopropylidene methyls), 1.24 (d, J=6.1 Hz, H-7). $^{13}$C NMR ($CDCl_3$) δ: 135.4, 116.5, 108.7, 108.4, 96.43, 72.8, 70.9, 70.7, 70.6, 70.4, 70.3, 26.04, 25.97, 24.9, 24.3, 17.2. Anal. calcd for $C_{16}H_{26}O_6$: C, 61.15, H, 8.28; Found: C, 61.10; H, 8.32.

3b, $[\alpha]_D^{25}$–73.5±2° (C 1.03 $CHCl_3$). $^1$H NMR ($CDCl_3$) δ: 5.94 (m, Ca=C), 5.57 (d, J=4.9 Hz, H-1), 5.31–5.11 (m, $CH_2$=C), 4.56 (dd, J=2.4, 8.2 Hz, H-3), 4.28 (dd, J=2.4, 5.2 Hz, H-2 ), 4.22 (dd, H-4 ), 4.20–4.05 (m, $OCH_2$—C=), 3.68 (m, H-5 and H-6), 1.53, 1.44 and 1.32 and 1.31 (isopropylidene methyls), 1.24 (d, J=6.1 Hz, H-7). $^{13}$C NMR ($CDCl_3$) δ: 135.8, 116.1, 109.1, 108.5, 96.4, 74.5, 72.2, 71.4, 70.9, 70.8, 70.4, 26.0, 25.9, 4.9, 24.4, 16.6. Anal. calcd for $C_{16}H_{26}O_6$: C, 61.15, H, 8.28; Found: C, 61.0; H, 8.27.

EXAMPLE 2

Synthesis of (2-Trimethylsilyl) ethyl 2,3,4-tri-O-benzyl-7-deoxy-β-D-glycero-D-galactoheptopyranoside (11a)

To an ice cold solution of 3a (11.2 g) in dichloromethane (150 ml), 90% aqueous trifluoroacetic acid (75 ml) was added. After 60 min, the solvents were evaporated and the residue was dissolved in acetic anhydride (75 ml) and pyridine (100 ml) containing 4-N,N-dimethylaminopyridine (10 mg). After 16 h, the reaction mixture was poured over ice and the product was extracted with dichloromethane. The dichloromethane layer was washed with ice cold hydrochloric acid (1 M) and saturated sodium bicarbonate solution. The solution was dried over anhydrous magnesium sulfate and the solvent was evaporated to get a syrup (compound 6a, 11 g) . A portion of the syrup (5 g) was dissolved in DMF (100 ml) containing acetic acid (0.9 g) and hydrazine (0.5 g) and heated to 50° C. for 2 h under dry nitrogen. The solvent was then evaporated and the residue was dissolved in dichloromethane. The dichloromethane layer was washed with ice cold hydrochloric acid (0.5 M) and saturated sodium bicarbonate solution. The solution was dried over anhydrous magnesium sulfate and the solvent was evaporated to get a syrup (3.8 g).

The above syrup (3.8 g) was dissolved in dichloromethane (100 ml). 2,4,6-Trimethylpyridine (s-collidine, 1.3 g) and Viismeier bromide (4.8 g) were added and stirred for 2 h. The reaction mixture was then washed with water, ice cold hydrochloric acid (0.5 M) and saturated sodium bicarbonate solution. The solution was dried over anhydrous magnesium sulfate and the solvent was evaporated. Purification by chromatography on a column of silica gel using ethyl acetate—hexane (1:5) gave pure 6-O-allyl-2,3,4-tri-O-acetyl- 7-deoxy-α-D-glycero-D-galactoheptopyranosyl bromide (7a, 2.9 g) . $^1$H NMR ($CDCl_3$) δ: 6.71 (d, H-1), 5.79 (m, —CH=C) , 5.74 (d, H-4) , 5.38 (dd, H-3) , 5.26–5.13 (m, $CH_2$=C), 5.02 (dd, H-2), 4.03 and 3.76 (m, O—$CH_2$—C=), 4.00 (dd, H-5), 3.55 (m, H-6), 2.14, 2.11 and 2.00 (3 s, $CH_3COO$), 1.20 (d, H-7).

To a cold solution (–28° C.) of 2-(trimethylsilyl)-ethanol (9.1 g) in nitromethane (100 ml) containing silver trifluoromethanesulfonate (2.0 g) and s-collidine (0.65 g), a solution of 7a (2.9 g) in dichloromethane (30 ml) was added in drops. After I h at –28° C. the reaction mixture was diluted with dichloromethane and filtered. The filtrate was washed with water, 5% sodium thiosulfate solution, ice cold hydrochloric acid (0.5 M) and saturated sodium bicarbonate solution. The solvent was removed under reduced pressure to give a homogeneous syrup (3.3 g), which was identified by NMR as (2-trimethylsilyl) ethyl 2,3,4-tri-O-acetyl-7-deoxy-β-D-glycero-D-galactoheptopyranoside (8a). $^1$H NMR ($CDCl_3$) δ: 5.78 (m, 1H, —CH=C—), 5.61 (dd, J=1.0, 3.4 Hz, H-4) , 5.25–5.10 (m, 3H, $CH_2$=C, H-2), 5.00 (dd, J=3.4, 10.4 Hz, H-3), 4.44 (d, J=7.9 Hz, H-1), 4.1–3.5 (m, 5H, O—$CH_2$ of aglycon, O—$CH_2$—C=, H-6), 3.34 (dd, J=1.1, 8.8 Hz, H-5), 2.13, 2.03 and 1.97 (3 s, $CH_3COO$), 1.25 (d, J=6.0 Hz, H-7). Compound 8a was dissolved in dry methanol (50 ml) containing sodium methoxide solution (0.5 M, 0.8 ml) and stirred for 16 h. The reaction mixture was then neutralized with H+ resin, filtered and evaporated to get a solid (2.6 g). This was dissolved in dry DMF (50 ml) containing sodium hydride (1.2 g) followed by the addition of benzyl bromide (8.5 g). After 2 h, methanol (3 ml) was added and the solvent was evaporated. The residue was extracted with dichloromethane and washed with water, ice cold hydrochloric acid (0.5 M) and saturated sodium bicarbonate solution. Purification by chromatography on a column of silica gel using ethyl acetate—hexane (1:12) gave pure 2-(trimethylsilyl)ethyl 6-O-allyl- 2,3,4-tri-O-benzyl-7-deoxy-β-D-glycero-D-galactoheptopyranoside (10a, 3.1 g). $^1$H NMR ($CDCl_3$) δ: 7.4–7.2 (m, aromatic hydrogens), 5.86 (m, —CH=C), 5.26–5.10 (4 m, 2H, $CH_2$=C), 5.04–4.61 (6 benzylic hydrogens), 4.34 (d, J-7.7 Hz, H-1), 4.14 (d, J=2.3 Hz, H-4), 4.1–3.5 (O—$CH_2$ of aglycon, O—$CH_2$C=, H-3, H-2 and H-6), 3.07 (dd, J=0.7, 8.9 Hz, H-5), 1.24 (d, J=6.0 Hz, H-7), 1.04 (dd, $CH_2$Si).

A solution of 10a (8.45 g) in dry tetrahydrofuran (THF, 100 ml) containing 1,5-cyclooctadiene-bis(diphenylmethylphosphine)-iridium hexafluorophosphate (300 mg) was gently evacuated and equilibrated under nitrogen pressure twice, followed by brief exposure to hydrogen for 10 min. The reaction mixture was stirred under nitrogen atmosphere for 16 h. The solvent was evaporated and the residue was dissolved in 90% aqueous acetonitrile (220 ml) containing lithium bromide (7.2 g) and acetonitrile washed H+ resin (7.2 g) . After 15 min, the solution was filtered, neutralized with triethylamine, the solvent was evaporated and the residue was dissolved in dichloromethane. The dichloromethane was washed with water, ice cold hydrochloric acid (0.5 M) and saturated sodium bicarbonate solution, dried over anhydrous magnesium sulfate and evaporated. The product was purified on a column of silica gel using ethyl acetate—hexane (1:6) as eluant to get pure 11a (4.5 g). $[\alpha]_D{}^{25}$–23.3±2° (C 0.97, $CHCl_3$). $^1H$ NMR ($CDCl_3$) δ: 7.40–7.28 (m, aromatic hydrogens), 5.01–4.72 (6 benzylic hydrogens), 4.33 (d, J=7.7 Hz, H-1), 4.01–3.5 (6 H, O—CH2— of aglycon, H-2, H-4, H-6 and H-3), 2.87 (dd, J=0.7, 8.3 Hz, H-5), 1.18 (d, J=6.3 Hz, H-7), 1.03 (m, $CH_2$—Si). $^{13}C$ NMR ($CDCl_3$) δ: 138.9, 138.5, 128.8, 128.5, 128.4, 128.2, 128.1, 127.6, 127.5, 103.5, 82.5, 79.7, 78.3, 75.1, 73.8, 73.3, 71.3, 67.0, 65.4, 20.3, 18.3, –1.5. Anal calcd for $C_{33}H_{44}O_6Si$: C, 70.28, H, 7.80; Found: C, 69.97; H, 7.92.

EXAMPLE 3

Synthesis of (2-Trimethylsilyl)ethyl 2,3,4-tri-O-benzyl-7-deoxy-α-L-glycero-D-galactoheptopyranoside (11b)

Compound 3b (34.5 g) was converted to 7b via 6b (yield of 6b from 3b was 20.5 g; 13.8 g of this was converted to 7b) according to the procedure described earlier for 7a. Purification of the crude product by chromatography on a column of silica gel using ethyl acetate—hexane (1:5) gave pure 6-O-allyl-2,3,4-tri-O-acetyl- 7 -deoxy-β-L-glycero-D-galactoheptopyranosyl bromide (7b, 11.4 g). $^1H$ NMR ($CDCl_3$) δ: 6.76 (d, J=4.2 Hz, H-1), 5.87 (m, —CH=C—), 5.52 (broad d, J=2.2 Hz, H-4), 5.36 (dd, J=3.2, 10.7 Hz, H-3), 5.28–5.14 (m, $CH_2$=C), 5.04 (dd, J=3.9, 10.5 Hz, H-2), 4.14 (d, J=7.3 Hz, H-5), 4.03 (m, O—$CH_2$—C=), 3.64 (m, H-6), 2.13, 2.11 and 2.0) 3 s, $CH_3COO$), 1.11 (d, J=6.6 Hz, H-7 ) .

Compound 7b (11.4 g) was converted to 8b according to the procedure described for 8a. Purification on a column of silica gel using ethyl acetate—hexane (1:4) as eluant, gave pure 2-(trimethylsilyl)ethyl 6-O-allyl- 2,3,4-tri-O-acetyl-7-deoxy-(α-L-glycero-D-galactoheptopyranoside (8b, 9.8 g). $^1H$ NMR ($CDCl_3$) δ: 5.89 (m, CH=C), 5.36 (dd, J=0.8, 3.4 Hz, H-4), 5.3–5.1 (m, $CH_2$=C), 5.18 (dd, J=8.0, 10.4 Hz, H-2), 4.97 (dd, J=3.4, 10.4 Hz, H-3), 4.45 (d, J=8.0 Hz, H-1), 4.15 (m, O—$CH_2$—C=), 4.0–3.6 (m, O—$CH_2$ of aglycon, H-6), 3.50 (dd, J=0.9, 7.9 Hz, H-5), 2.14, 2.04 and 1.96 (3 s, $CH_3COO$), 1.08 (d, J=6.3, H-7).

Compound 8b ( 9.8 g) was converted to 11b as described earlier for 11a. The product was purified on a column of silica gel using ethyl acetate—hexane (1:4) as eluant to get pure 11b (4.5 g). $[\alpha]_D{}^{25}$–5.0±2° (c 1.04, $CHCl_3$). $^1H$ NMR ($CDCl_3$) δ: 7.4–7.2 (m, aromatic hydrogens), 5.00–4.63 (benzylic hydrogens), 4.37 (d, J=7.8 Hz, H-1), 4.0 and 3.58 (m, O—$CH_2$— of aglycon and H-6), 3.83 (dd, J=7.8, 9.8 Hz, H-2), 3.77 (d, J=2.2 Hz, H-4), 3.51 (dd, J=2.9, 9.8 Hz, H-3), 2.97 (d, J=7.6 Hz, H-5), 1.04 (m, $CH_2$—Si), 0.87 (d, J=6.4 Hz, H-7). $^{13}C$ NMR ($CDCl_3$) δ: 138.7, 138.4, 138.1, 128.5, 128.4, 128.3, 128.2, 128.1, 127.8, 127.6, 127.52, 127.49, 103.6, 82.9, 79.5, 78.8, 75.1, 74.1, 73.54, 73.48, 67.5, 66.7, 18.5, 17.7, –1.5. Anal. calcd for $C_{33}H_{44}O_6Si$: C, 70.28, H, 7.80; Found: C, 69.97; H, 7.92.

EXAMPLE 4

Synthesis of Methyl (methyl 5-acetamido-3,5dideoxy-4,7,8,9-tetra-O-acetyl-2-thio-α-D-glycero-D-galacto-nonulopyranosid)onate (12b)

N-Acetylneuraminic acid (20 g) was converted to methyl 5-acetamido-3,5-dideoxy-2,4,7,8,9-penta-O-acetyl-β -D-glycero-D-galactononulopyranosylonate (31.3 g, crude) according to the literature methods. (Baggert, N. et al., *Carbohydr. Res.* 1982, 110, 11–18; Hasegawa, A. et al., *Carbohydr. Res.* 1991, 212, 277–281). A portion of this (5.0 g) was dissolved in glacial acetic acid (50 mL) containing acetic anhydride (2 mL) and anhydrous HCl gas was gently bubbled (45 min) into the solution. After 16 h, the reaction mixture was worked up and the crude product (12a) (4.8 g) was dissolved in acetonitrile (50 mL) containing sodium thiomethylate (0.82 g). After 2 h, the solvent was evaporated and the residue dissolved in $CH_2Cl_2$ and washed with water, ice cold 1 M HCl and saturated sodium bicarbonate solution. The crude product 12b (4.3 g) obtained by this short procedure was greater than 90% pure as evidenced from the $^1H$ NMR spectrum. The NMR parameters were identical to those published by Hasegawa et al. (*J. Carbohydr. Chem.* 1986, 5, 11–19). This crude product was employed in subsequent glycosylation reactions.

EXAMPLE 5

Synthesis of Sodium salt of 5-acetamido-3,5-dideoxy-D-glycero-D-galacto-nonulopyrano-sylonate( 2-6)-7-deoxy-β-D-glycero-D-galactohepto-pyranosyl-OCH $_2CH_2Si(CH_3)_3$ (16a)

To a cold (–50° C.) solution of 11a (601 mg), 12b (1.12 g) and silver trifluoromethanesulfonate (590 mg) in 5:3 mixture of acetonitrile-propiononitrile (40 ml) containing powdered 3Å molecular sieves (2.1 g), methylsulfenyl bromide solution in 1,2-dichloroethane (1 M, 2.4 ml) was added in drops. After 18 h at –50° C., the reaction mixture was warmed to room temperature followed by the addition of saturated sodium bicarbonate solution (3 ml). The reaction mixture was filtered through a pad of Celite and the residue was washed with dichloromethane. The filtrate was washed with water, ice cold hydrochloric acid (0.5 M) and saturated sodium bicarbonate solution. The solvent was then evaporated and the products were isolated by chromatography using ethyl acetate—hexane-ethanol (10:15:1) as eluant. About 260 mg of 11a was recovered and the products were eluted in the following order. β-Anomer of 14a (60 mg); β+14a mixture (190 mg); 14a (320 mg), Compound 13 (490 mg). This procedure was repeated to obtain a larger amount of 14a. The structure of 14a was confirmed by NMR. $[\alpha]_D{}^{25}$+1.6±2° (c 1.02, $CHCl_3$) $^1H$ NMR ($CDCl_3$) δ: 7.37–7.25 (aromatic hydrogens), 5.30 (m, H-7' and H-8' ), 5.11 (d, J=9.9 Hz, NH), 5.10–4.72 ( 6 d, benzylic hydrogens), 4.81 (m, H-4'), 4.31 (d, J=7.7 Hz, H-1), 3.49 (dd, J=2.6, 9.5 Hz, H-3), 3.42 (s, $COOCH_3$), 3.11 (d, J=7.7 Hz, H-5), 2.64 (dd, J=4.7, 12.8 Hz, H-3eq), 2.14–1.88 (5×s, 4 OAc and 1 NHAc), 1.97 (t, J=12.5 Hz, H-$3_{ax}$), 1.33 (d, J=6.2 Hz, H-7), 1.02 (dd, 2 H, —$CH_2$Si). $^{13}C$ NMR ($CDCl_3$) δ: 170.9, 170.6, 170.2, 170.11, 170.08, 167.4, 139.3, 138.8, 138.6, 128.3, 128.2, 128.1, 128.0, 127.4, 127.0, 126.9, 103.7, 100.2, 82.5, 79.5, 77.2, 75.0, 73.9, 73.4, 73.0, 72.7, 72.1, 69.5, 69.0, 67.5, 67.3, 62.1, 52.8, 49.4, 39.1, 23.2, 21.0, 20.9, 20.8, 20.7, 18.9, 18.4, –1.5. Anal. calcd for $C_{53}H_{71}O_{19}NSi$: C, 60.4; H, 6.7, N, 1.3. Found: C, 60.46; H, 6.78; N, 1.41.

Compound 14a (439 mg) was dissolved in 90% aqueous ethanol (80 ml) containing 20% palladium hydroxide on carbon (300 mg) and gently evacuated and equilibrated under hydrogen atmosphere. After 4 h, the reaction mixture was filtered through a pad of Celite and the filtrate was concentrated to a dry residue. This was dissolved in dry methanol (30 ml) followed by the addition of sodium methoxide solution (0.5 M, 0.25 ml). After 4 h, the solution was neutralized with H+ resin, filtered and the filtrate was evaporated to a dry residue. This was redissolved in water and lyophilized to get a colorless material (254 mg). A portion of this material (244 mg) was dissolved in deionized water (10 ml) containing Chelex resin (sodium form, 200–400 mesh, 1.02 g) and stirred at room temperature for 24 h. Additional resin (1.1 g) and water (5 ml) were added and the reaction was continued for additional 24 h. The resin was then filtered through a pad of Celite and the filtrate was lyophilized to get a residue (240 mg) which was homogeneous on tlc (ethyl acetate-ethanol-water= 4:2:1). This was dissolved in water and applied to a column of Bio Gel P-2 (200–400 mesh, 1400 ml), equilibrated and eluted with deionized water. The fractions (7.5 ml) containing the product (as evidenced by U.V. absorption at 220 nm), were pooled and lyophilized to get a colorless product 16a (224 mg). $[\alpha]_D^{25}$–22.5±2°, (C 0.99, $H_2O$). $^1$H NMR (see Table 1). $^{13}$C NMR (see Table 2). Anal. calcd for $C_{23}H_{42}O_{14}NSiNa.2H_2O$: C, 42.92; H, 7.15; N, 2.18. Found: C, 42.21; H, 7.21; N, 2.37.

TABLE 1

$^1$H chemical shifts (500.13 or 600.13 MHz) for the "tg" and "gt" sialosides (15a, 15b, 16a, 16b, 16d, 22a, and 22b) in $D_2O$ at 300° K
The chemical shifts are expressed relative to internal acetone (2.23 ppm) which sets the HDO signal at 4.75 ppm.
The proton-proton couplings constants in Hz are given in parenthesis

| | Hydrogen | | | | | | 22a | | 22b | |
|---|---|---|---|---|---|---|---|---|---|---|
| Units | Atom | 15a | 15b | 16a | 16b | 16d | α-OH | β-OH | α-OH | β-OH |
| αDNeuAc | H3'ax | 1.94 (11.7, 13.0) | 1.91 (12.9, 12.2) | 1.74 (12.5, 12.0) | 1.64 (12.4, 12.2) | 1.67 (12.2) | 1.77 (12.5, 11.2) | | 1.73 (12.0) | 1.75 (12.0) |
| | H3'eq | 2.73 (4.6) | 2.63 (4.5) | 2.77 (4.7) | 2.73 (4.5) | 2.73 (4.6) | 2.80 (4.7) | 2.79 (4.7) | 2.79 (4.5) | 2.80 (4.5) |
| | H4' | 3.78 (10) | 3.73 (11) | 3.70 (10.0) | 3.65 (10.0) | 3.65 (10.0) | 3.68 (10.0) | | 3.67 | |
| | H5' | 3.87 (10.4) | 3.86 (10.2) | 3.81 (10.3) | 3.78 (10.0) | 3.79 (10.0) | 3.79 (10.2) | | 3.80 (10.4) | |
| | H6' | 3.71 (1.1) | 3.69 (0.6) | 3.66 (1.8) | 3.56 | 3.58 | 3.57 | | 3.59 (1.7) | |
| | H7' | 3.56 (9.2) | 3.54 (9.0) | 3.59 (9.0) | 3.57 (10) | 3.58 | 3.57 (10) | | 3.56 (9.6) | |
| | H8' | 3.80 | 3.85 | 3.84 | 3.89 | 3.88 | 3.83 | | 3.87 | |
| | H9a' | 3.86 (12.0, 2.5) | 3.84 (11.9) | 3.88 (12.5, 2.5) | 3.86 (11.4, 2) | 3.87 | 3.84 (12.0. 2.4) | | 3.86 (12.0. 2.5) | |
| | H9b' | 3.67 (6.0) | 3.65 (6.0) | 3.65 (6.0) | 3.63 (6.1) | 3.63 | 3.62 (6.1) | | 3.62 (6.5) | |
| | NAC | 2.05 | 2.01 | 2.05 | 2.01 | 2.01 | 2.02 | | 2.02 | |
| | $COOCH_3$ | 3.87 | 3.85 | | | | | | | |
| βDGal | H1 | 4.39 (8.0) | 4.29 (7.9) | 4.38 (7.9) | 4.32 (7.9) | 4.23 (8.0) | 5.20 (3.4) | 4.50 (7.9) | 5.22 (2.3) | 4.52 (7.8) |
| | H2 | 3.48 (9.8) | 3.46 (9.8) | 3.48 (9.9) | 3.48 (9.8) | 3.50 (9.9) | 3.76 | 3.44 (9.9) | 3.79 | 3.48 (10.0) |
| | H3 | 3.58 (3.5) | 3.58 (3.4) | 3.60 (3.5) | 3.58 (3.3) | 3.59 (3.5) | 3.76 | 3.56 (3.5) | 3.79 | 3.56 (3.3) |
| | H4 | 4.09 (<1) | 3.92 (<1) | 4.13 (<1) | 3.98 (<1) | 4.00 (<1) | 4.22 | 4.17 (<1) | 4.11 | 4.10 (<1) |
| | H5 | 3.28 (8.6) | 3.34 (8.5) | 3.28 (8.6) | 3.33 (6.5) | 3.36 (6.0) | 3.77 (8.4) | 3.38 | 3.80 (8.8) | 3.46 (7.9) |
| | H6 | 4.30 (6.2) | 4.45 (6.4) | 4.13 (6.2) | 4.48 (6.3) | 4.49 (6.4) | 3.35 (6.9) | 3.39 (6.6) | 3.40 (7.2) | 3.42 (7.1) |
| | H7 | 1.34 | 1.18 | 1.36 | 1.16 | 1.18 | 1.42 | 1.44 | 1.31 | 1.33 |
| aglycon | OMe | | | | | 3.57 | | | | |
| | OCHa | 3.97 | 4.00 (10.1. 13.0 5.2)) | 3.96 (10.0, 12.5, 5.3) | 4.03 (10.3, 13.0, 5.4) | | | | | |
| | OCHb | 3.76 | 3.75 (5.3, 13.0) | 3.75 (5.5, 12.5) | 3.77 (5.2. 13.0) | | | | | |
| | SiCHa | 1.07 | 1.08 (13.0) | 1.06 (13.2) | 1.07 (13.0) | | | | | |
| | SiCHb | 0.97 | 0.99 | 0.97 | 1.00 | | | | | |
| | $SiCH_3$ | 0.03 | 0.04 | 0.02 | 0.03 | | | | | |

TABLE 2

$^{13}$C chemical shifts (125.76 MHz) for the "tg" and "gt" sialosides (15a, 15b, 16a, 16b, 16d, 22a, and 22b) in $D_2O$ at 300°K
The chemical shifts are expressed relative to 1,4-Dioxane (66.9 ppm) using the deuterium lock of the spectrometer.
The Tl's (sec.) are given in parenthesis
The values in brackets are selected $^1$H-$^{13}$C coupling constants in Hz

| | Carbon | | | | | | 22a | | 22b | |
|---|---|---|---|---|---|---|---|---|---|---|
| Units | Atom | 15a | 15b | 16a | 16b | 16d | α-OH | β-OH | α-OH | β-OH |
| αDNeu-Ac | C1' | 169.8 | 170.7 | 173.9 [5.6] (2.8) | 174.4 [5.6] (2.9) | 174.3 [5.6] | 174.75 | | 174.7 | 174.6 |
| | C2' | 100.3 | 99.4 | 102.3 (3.7) | 99.9 (5.0) | 100.2 | 87.3 | 87.4 | 85.7 | 86.2 |
| | C3' | 38.5 | 38.9 | 40.4 (0.21) | 41.0 (0.17) | 40.8 | 41.61 | 41.56 | 41.48 | 41.54 |
| | C4' | 67.6 | 67.6 | 67.6 (0.41) | 68.55 (0.35) | 68.7 | 68.8 | | 68.8 | |
| | C5' | 51.9 | 52.1 | 52.1 (0.33) | 52.2 (0.35) | 52.2 | 52.0 | | 52.0 | |

TABLE 2-continued $^{13}C$ chemical shifts (125.76 MHz) for the "tg" and "gt" sialosides (15a, 15b, 16a, 16b, 16d, 22a, and 22b) in $D_2O$ at 300°K
The chemical shifts are expressed relative to 1,4-Dioxane (66.9 ppm) using the deuterium lock of the spectrometer.
The Tl's (sec.) are given in parenthesis
The values in brackets are selected $^1H$-$^{13}C$ coupling constants in Hz

| | Carbon | | | | | | 22a | | 22b | |
|---|---|---|---|---|---|---|---|---|---|---|
| Units | Atom | 15a | 15b | 16a | 16b | 16d | α-OH | β-OH | α-OH | β-OH |
| | C6' | 73.1 | 73.3 | 73.2 (0.35) | 73.0 (0.34) | 73.0 | 75.3 | | 75.1 | 75.2 |
| | C7' | 68.4 | 68.6 | 68.44 | 68.58 (0.33) | 68.6 | 68.4 | | 68.6 | |
| | C8' | 71.0 | 71.1 | 72.3 (0.34) | 72.1 (0.36) | 72.2 | 72.4 | | 72.2 | 72.4 |
| | C9' | 63.4 | 63.4 | 63.0 (0.26) | 62.9 (0.24) | 62.9 | 62.9 | | 63.0 | |
| | $NHCOCH_3$ | 22.4 | 22.4 | 22.3 (1.0) | 22.3 (1.4) | 22.4 | 22.3 | | 22.3 | |
| | NHCO | 175.2 | 175.3 | 175.4 (2.2) | 175.4 (2.2) | 175.4 | 175.3 | | 175.3 | |
| | $COOCH_3$ | 53.7 | 53.8 | | | | | | | |
| βDGal | C1 | 102.6 | 102.1 | 102.5 (0.42) | 102.5 (0.37) | 104.3 | 92.7 | 97.1 | 92.6 | 97.0 |
| | C2 | 71.1 | 71.0 | 71.2 (0.35) | 71.2 (0.37) | 71.1 | 68.7 | 72.2 | 68.7 | 72.2 |
| | C3 | 73.5 | 73.5 | 73.2 (0.35) | 73.5 (0.36) | 73.4 | 69.9 | 73.3 | 70.1 | 73.6 |
| | C4 | 67.7 | 68.9 | 68.0 (0.37) | 69.7 (0.34) | 69.8 | 69.5 | 69.1 | 69.6 | 69.1 |
| | C5 | 77.2 | 77.5 | 77.7 (0.36) | 77.2 (0.35) | 77.1 | 72.7 | 77.5 | 72.0 | 76.6 |
| | C6 | 68.9 | 70.6 | 69.8 (0.29) | 70.3 (0.33) | 70.4 | 39.6 | 39.4 | 39.7 | 40.2 |
| | C7 | 19.3 | 17.8 | 19A (0.98) | 17.2 (0.55) | 17.5 | 20.7 | 20.5 | 18.9 | 18.6 |
| aglycon | OMe | | | | | 57.4 | | | | |
| | $OCH_2$ | 69.3 | 68.4 | 68.50 | 68.47 (0.43) | | | | | |
| | $SiCH_2$ | 17.8 | 17.8 | 17.9 (0.78) | 17.8 (0.69) | | | | | |
| | $SiCH_3$ | −2.2 | −2.2 | −2.2 (4.3) | −2.1 (4.3) | | | | | |

EXAMPLE 6

Synthesis of Sodium salt of 5-acetamido-3,5-dideoxy-D-glycero-D-galacto-nonulopyrano-sylonate( 2-6)-7-deoxy-α-L-glycero-D-galactohepto-pyranosyl-$OCH_2CH_2Si(CH_3)_3$ (16b)

To a cold (−50° C.) solution of 11b (895 mg), 12b (1.68 g) and silver trifluoromethanesulfonate (885 mg) in 5:3 mixture of acetonitrile-propiononitrile (40 ml) containing powdered 3Å molecular sieves (2.1 g), methylsulfenyl bromide solution in 1,2-dichloroethane (1 M, 3.5 ml) was added in drops. Work up and purification as described above for 14a, gave compound 14b (530 mg); mixture of 14b and its β-anomer (190 mg); compound 13 (870 mg). This procedure was repeated to obtain more 14b. Its structure was confirmed by NMR. $[\alpha]_D{}^{25}$−9.1±2° (c 1.04, $CHCl_3$) $^1H$ NMR ($CDCl_3$) δ: 7.38–7.26 (aromatic hydrogens), 5.30 (m, 2 H, H-7' and H-8'), 5.10 (d, J=9.9 Hz, 1 H, NH—), 5.04–4.64 (6×d, benzylic hydrogens), 4.89 (m, H-4'), 4.35 (d, J=7.7 Hz, H-1), 4.22 (m, 1H, H-6), 3.77 (s, 3H, $COOCH_3$), 3.51 (dd, J=2.6, 9.5 Hz, H-3), 3.25 (d, J=7.7 Hz, H-5), 2.49 (dd, J=4.8, 13.2 Hz, H-3'eq), 2.13 (t, J=12.5 Hz, H-$3_{ax}$), 2.12–1.88 (5×s, 4×OAc and NHAc), 1.03 (d, J=6.2 Hz, H-7), 0.00 {$(CH_3)_3Si$}. $^{13}C$ NMR ($CDCl_3$) δ: 170.9, 170.6, 170.2, 170.0, 169.8, 168.4, 138.9, 138.6, 138.5, 128.4, 128.3, 128.24, 128.18, 128.15, 129.1, 127.5, 127.50, 127.4, 103.3, 99.5, 83.4, 79.6, 76.2, 75.0, 73.9, 73.7, 73.5, 72.6, 70.7, 69.2, 68.8, 67.5, 67.0, 62.3, 52.8, 49.4, 36.7, 23.1, 21.0, 20.8, 18.3, 17.9, −1.5. Anal. calcd for $C_{53}H_{71}O_{19}NSi$: C, 60.4; H, 6.7, N, 1.38. Found: C, 60.33; H, 6.80; N, 1.38.

Compound 14b (955 mg) was converted to 16b (514 mg) as described for 16a. An analytical sample was prepared by filtration of a portion of the residue (118 mg) on a column of Bio Gel P-2 (200–400 mesh, 1400 ml) equilibrated and eluted with deionized water. The fractions (7.5 ml) containing the product (as evidenced by U.V. absorption at 220 nm), were pooled and lyophilized to get a colorless product 16b (101 mg). $[\alpha]_D{}^{25}$−28.6±2° (c 1.0, $H_2O$). $^1H$ NMR (Table 1). $^{13}C$ NMR (see Table 2). Anal. calcd for $C_{23}H_{42}O_{14}NSiNa.2H_2O$: C, 42.92; H, 7.15; N, 2.18. Found: C, 42.46; H, 7.38; N, 2.17.

EXAMPLE 7

Synthesis of Sodium salt of 5-acetamido-3,5-dideoxy-D-glycero-D-galacto-nonulopyranosylonic acid (2-6)-1,2;3,4-di-O-isopropylidene-7-deoxy-α-D-glycero-D-galactohepto-pyranose (19a)

To a suspension of 2a (548 mg, 2 mmol), glycosyl xanthate 12c (1.487 g, 2.5 mmol), silver triflate (642 mg), and 3Å molecular sieves (3.0 g) in 1:1 acetonitrile-propionitrile mixture (50 ml) at −50° C., methylsulfenyl bromide solution (1 M in 1,2-dichloroethane, 3 ml) was added After 18 h at −50° C. the reaction mixture was worked up as described for 14a and the product was purified by chromatography using ethyl acetate-ethanol-water (10:15:1) as eluant. The products were eluted in the following order: the starting alcohol 2a (230 mg), the β-anomer of 17a (50 mg), a mixture of β and α-sialoside (400 mg), a 2:3 mixture of α-sialoside (17a) and glycal 13 {700 mg, the ratio of 17a and 13 was determined by the integarations of nmr signals at 2.68 (H-3' eq) ppm for 17a and 6.1 ppm (H-3') for 13, the α-anomeric configuration of 17a was confirmed by identification of H-4' signal at 4.83 ppm} and pure 13 (140 mg). The mixture of 17a and 13 (700 mg) was de-O-acetylated with NaOMe (0.5 M, 0.2 ml) and methanol (20 ml, 36 h), and the crude product was applied to a column of Bio Gel P-2. The disaccharide 18a which eluted first (218 mg) was converted to the sodium salt 19a (219 mg) by Chelex resin as described earlier. $[\alpha]_D{}^{25}$−26.9±2°, (c 1.0, $H_2O$). $^1H$ NMR ($D_2O$) δ: 5.56 (d, J=5.0 Hz, H-1), 4.65 (dd, J=2.2, 7.9 Hz, H-3), 4.44 (dd, J=1.5, 7.9 Hz, H-4), 4.40 (dd, J=2.0, 5.0 Hz, H-2), 4.23 (m, H-6), 3.82–3.76 (m, 2H, H-8', H-9') 3.73 (t, J=10.3 Hz, H-5'), 3.69 (dd, J=1.3, 5.9 Hz, H-7'), 3.58 (m, H-4 '), 3.56 (dd, H=6.8, 12.6 Hz, H-9'), 3.48–3.52 (m, 2H, H-6 ' and H-5), 2.69 (dd, J=4.6 Hz, 12.5 Hz, H-3'eq), 1.96 (s, NAc), 1.61 (t, J=12.3 Hz, H-3'ax), 1.52, 1.39, 1.32 & 1.31 (4×s, isopropylidene methyls), 1.23 (d, J=6.4 Hz, H-7). $^{13}C$ NMR ($D_2O$) δ: 174.9, 172.6, 109.61, 109.59, 101.3, 95.8, 72.4, 71.8, 70.6, 70.2, 70.1, 70.0, 69.8, 68.3, 67.9, 62.4, 51.6, 40.2, 24.9, 24.6, 23.9, 22.9, 21.9, 18.1. Anal. Calcd for $C_{24}H_{38}O_{14}NNa.3H_2O$: C, 44.92; H, 6.86; N, 2.18: Found: C, 44.00; H, 6.77; N, 2.13.

EXAMPLE 8

Synthesis of Sodium salt of 5-acetamido-3,5-dideoxy-D-glycero-D-galacto-nonulopyranosylonic acid (2-6)-1,2;3,4-di-O-isopropylidene-7-deoxy-α-D-glycero-D-galactohepto-pyranose (19b)

To a suspension of 2b (600 mg, 2.2 mmol), thioglycoside 12b (1.14 g), and 3Å molecular sieves (1.5 g) in 2:1 acetonitrile-propiononitrile mixture (24 ml) at –50° C., dimethyl (methylthio) sulfonium triflate (1.50 g) solution in $CH_3CN$ (10 ml) was added over a period of 10 min After 3 days at –35° C. the reaction mixture was worked up as described for 14a and the product was purified by chromatography using $CH_2Cl_2$—MeOH (30:1) as eluant. After the starting material (420 mg), a homogeneous product (1.20 g) was eluted. $^1$H NMR showed that the product was a mixture of the sialoside 17b and the glycal 13 (17b: 13=15:4), along with minor β-sialosides. This mixture was treated with sodium methoxide (0.5 ml) in methanol (20 ml) and worked up after 18 h. Yield 670 mg. A portion (115 mg) of this was dissolved in deionized water (5 ml) and applied to a column of Bio Gel P-2 and fractions (7.5 ml) were collected. The disaccharide appeared in fractions 84–95. These fractions were pooled and lyophilized to obtain 18b (34 mg), contaminated with minor amounts (<20%) of the β-anomer. This was then converted to the sodium salt 19b as described earlier $[\alpha]_D^{25}$–35.1±2°, (c 1.0, $H_2O$). $^1$H NMR ($D_2O$) δ: 5.80 (d, J=5.1 Hz, H-1), 4.70 (dd, J=2.4, 7.9 Hz, H-3), 4.47(dd, J=2.6, 5.1 Hz, H-2), 4.41 (dd, J=1.8, 7.9 Hz, H-4), 4.35 (m, H-6), 3.82 (m, H-8', H-9'), 3.78 (t J=9 7 Hz, H-5'), 3.62–3.50 (m,) H-4', H-6', H-7', H-9' and H-5), 2.64 (dd, J=4.6, 12.3 Hz, H-3'eq), 1.95 (s, NAc), 1.63 (t, J=12.1 Hz, H-3 'ax), 1.51, 1.42 and 1.32 (3×s, isopropylidene methyls), 1.12 (d, J=6.2 Hz, H-7). $^{13}$C NMR ($D_2O$) δ: 175.3, 174.5, 110.3, 110.2, 110.14, 110.09, 99.6, 96.5, 72.9, 72.2, 71.2 (2×C), 70.6, 70.0, 69.6, 68.8, 68.5, 62.7, 52.1, 40.8, 25.5, 25.2, 24.3, 23.8, 22.4, 16.7.

EXAMPLE 9

Sodium salt of 5-acetamido-3,5-dideoxy-D-glycero-D-galacto-nonulopyranosylonic acid( 2-S-6)-7 -deoxy-D-glycero-D-galactoheptopyranose (22a)

To a solution of 2b (7.8 g) in $CH_2Cl_2$ (150 ml) at 0° C., pyridine (10 mL) and trifluoromethanesufonic anhydride (10.2 g) were added and the reaction mixture was stirred at 0° C. for 1 h. The reaction mixture was diluted with dichloromethane and washed with water, ice cold 1 M hydrochloric acid and saturated sodium bicarbonate solution. The solvent was evaporated and the crude product was dissolved in DMF (150 ml) containing potassium thioacetate (5.5 g, Janssen Chimica, New Brunswick, N.J.) and stirred at room temperature for 18 h. The solvent was evaporated and the residue was dissolved in dichloromethane and washed with water, ice cold 1 M hydrochloric acid and saturated sodium bicarbonate solution. Purification by chromatography on silica gel using ethyl acetate-hexane (1:12) afforded 6,7-dideoxy-1,2;3,4-di-O-isopropylidene-6-acetylthio-α-D-glycero-D-galactoheptopyranose (4a, 5.6 g). $^1$H NMR ($CDCl_3$) δ: 5.58 (d, H-1), 4.58 (dd, H-3), 4.37 (dd, H-4), 4.29 (dd, H-2), 3.88 (dd, H-5), 3.74 (m, H-6), 2.31 (s, S-Ac), 1.52, 1.45, 1.33 and 1.32 (isopropylidene methyls), 1.43 (d, H-7).

A portion of the above residue 4a (4.6 g) was dissolved in dry methanol (40 ml) at 0° C. containing 30% ammonium hydroxide (4.6 mL) and dithiothreitol (2.8 g). After 16 h at 0° C., the solvent was evaporated and the residue was dissolved in $CH_2Cl_2$, dried with anhydrous $MgSO_4$, and concentrated. Purification of the product by chromatography on a column of silica gel (ethyl acetate— hexane=1:20) afforded product 5a (3.3 g). $[\alpha]_D^{25}$ – 59.8±2°, (c 1.02, $CHCl_3$). $^1$H NMR ($CDCl_3$) δ: 5.54 (d, H-1), 4.65–4.59 (m, 2 H), 4.30 (dd, 1 H), 3.45 (dd, 1 H), 3.12 (m, H-6), 1.66 (d, SH), 1.4 (d, H-7), 1.53, 1.44, 1.35 & 1.33 (isopropylidene methyls). $^{13}$C NMR ($CDCl_3$) δ: 109.1, 108.6, 96.8, 73.6, 71.1, 70.97, 70.4, 33.63, 26.0, 25.9, 24.9, 24.4, 21.7. Anal. Calcd for $C_{13}H_{22}O_5S$: C, 53.79; H, 7.58: Found: C, 53.90; H, 7.71.

To a solution of 5a (3.0 g) in DMF (60 ml) at –20° C. sodium hydride (223 mg) was added After 10 min, a solution of 12a (4.74 g) in DMF (5 mL) was added and the solution was stirred at –20° C. for 16 hr. The solvent was evaporated and the residue was dissolved in $CH_2Cl_2$, washed with water, ice cold HCl (1 M) and saturated sodium bicarbonate solution, dried over anhydrous $MgSO_4$, and concentrated. Purification by chromatography on a column of silica gel (ethyl acetate— hexane-ethanol 10:10:1) gave a homogeneous product (5.5 g). $^1$H NMR showed it to be the desired product 20a contaminated with about 10% of 13. Pure 20a was made from this mixture by removal of the acetate groups with sodium methoxide in methanol, followed by gel permeation chromatography (see below) and then re-acetylation of the product with pyridine-acetic anhydride. $[\alpha]_D^{25}$ –8.1±2°, (c 0.98, $CHCl_3$). $^1$H NMR ($CDCl_3$) δ: 5.50 (d, J-5.1 Hz, H-1), 5.30 (m, 2H, H-7' and H-8' ), 5.12 (d, J=10.1 Hz, NH), 4.85 (m, H-4'), 4.50 (dd, J=2.4, 7.9 Hz, H-3), 4.36 (dd, J-1.7, 7.9 Hz, H-4), 4.29 (dd, J-2.2, 12.5 Hz, H-9'a), 4.26 (dd, J=2.6, 5.1 Hz, H-2), 4.12 (dd, J=4.6, 12.5 Hz, H-9'b), 4.03 (t, J=10.5 Hz, H-5'), 3.85 (dd, J=10.8 Hz, H-6'), 3.79 (s, $COOCH_3$), 3.50 (dd, J=1.5, 8.1 Hz, H-5), 3.30 (m, H-6), 2.74 (dd, J=4.8, 12.7 Hz, H-3'eq), 2.16, 2.13, 2.03, 2.02 and 1.87 (5× $CH_3CO$), 1.99 (H-3'ax), 1.46 (d, J=7.0 Hz, H-7), 1.49, 1.44, 1.32 and 1.31 (4 s, isopropylidene methyls). $^{13}$C NMR ($CDCl_3$) δ: 171.0, 170.6, 170.1, 169.9, 168.2, 109.4, 108.6, 96.7, 84.5, 74.4, 71.4, 71.1, 70.0, 69.0, 67.4, 62.1, 52.9, 49.4, 39.4, 38.4, 29.7, 26.0, 24.9, 24.8, 23.2, 21.3, 20.9, 20.8. Anal. Calcd for $C_{33}H49_{O17}SN$: C, 51.90; H, 6.42: Found: C, 49.23; H, 6.18.

This mixture of 20a and 13 (500 mg) was dissolved in methanol (20 ml) to which sodium methoxide solution (0.5 M, 0.2 ml) was added. After 4 h, the reaction mixture was neutralized with H+resin, filtered and the solvent evaporated. The residue was dissolved in 10% aqueous ethanol (5 ml) and applied to a column of Bio Gel P-2 (200–400 mesh, 1400 ml), equilibrated and eluted with water. The eluant was monitored by U.V. absorption at 220 nm. Fractions (7.5 ml) 77–84 were pooled and lyophilized to give methyl 5-acetamido-3,5-dideoxy-2 -thio-α-D-glycero-D-galacto-nonulopyranosylonate(2-S-6)- 6,7-dideoxy-1,2;3,4-di-O-isopropylidene-6-thio-α-D-glycero-D-galactoheptopyranose (21a) (280 mg). $[\alpha]_D^{25}$ 2.0±2°, (c 1.03, $H_2O$). $^1$H NMR ($D_2O$) δ: 5.56 (d, H-1), 4.66 (dd, H-3), 4.48 (dd, H-4), 4.44 (dd, H-2), 3.80 (s, $COOCH_3$), 3.62 (H-4'), 3.47 (H-5), 3.26 (m, H-5), 2.74 (dd, H-3eq), 1.95 (s, NAc), 1.78 (dd, H-$3_{ax}$), 1.47, 1.44, 1.32, 1.31 (isopropylidene methyls), 1.39 (d, H-7).

A solution of 21a (200 mg) in 50% aqueous trifluoroacetic acid (10 ml) was stirred at room temperature for 4 h and the solvent was evaporated. The residue was dissolved in water (5 ml) and applied to a column of Bio Gel P-2 (200–400 mesh, 1400 ml) equilibrated and eluted with water. The eluant was monitored by U.V. absorption at 220 nm. Fractions (7.5 ml) 108–121 were pooled and lyophilized to get the methyl ester of 22a (156 mg). $[\alpha]_D^{25}$ 50.9±2°, (c 1.05, $H_2O$). This was dissolved in water (10 mL) containing Chelex resin (sodium form, 200–400 mesh, 2 g) and stirred for 6 days. The resin was filtered and the solution was lyophilized to get obtain 22a as a colorless solid (87 mg) $[\alpha]_D^{25}$ +49.5±2°, (c 0.94 $H_2O$) $^1H$ and $^{13}C$ NMR data—see Tables 1 and 2. Anal. Calcd for $C_{18}H_{30}O_{13}SNa.2H_2O$: C, 38.64; H, 6.08; N, 2.50. Found: C, 38.83; H, 6.16; N, 2.57.

EXAMPLE 10

Synthesis of Sodium salt of 5-acetamido-3,5-dideoxy-2-thio-D-glycero-D-galacto-nonulopyranosylonic acid (2-S-6)-7-deoxy-L-glycero-D-galactoheptopyranose (22b)

To a solution of 2a (7.2 g) in $CH_2Cl_2$ (150 ml) at 0° C., pyridine (10 mL) and trifluoromethanesufonic anhydride (9.4 g) were added and the reaction mixture was stirred at 0° C. for 1 h. The reaction mixture was diluted with dichloromethane and washed with water, ice cold 1 M hydrochloric acid and saturated sodium bicarbonate solution. The solvent was evaporated and the crude product was dissolved in DMF (100 ml) containing potassium thioacetate (5.1 g) and stirred at 0° C. for 18 h. The product was worked up as described above for 4a. Purification by chromatography on silica gel using ethyl acetate-hexane (1:10) afforded 6,7-deoxy-1,2;3,4-di-O-isopropylidene-6-acetylthio-β-L-glycero-D-galaxtoheptopyranose (4b, 3.3 g) and 1,2;3,4-di-O-isopropylidene-α-D-galactohept-6-eneopyranose (4c, 3.2 g).

Data for 4b: $[\alpha]_D^{25}$ −52.7±2°, (c 1.05, $CHCl_3$). $^1H$ NMR of 4b ($CDCl_3$) δ: 5.54 (d, J=4.9 Hz, H-1), 4.61 (dd, J=5.4, 7.8 Hz, H-3), 4.32–4.29 (m, H-2, H-4), 3.77 (m, H-6), 3.68 (dd, J=1.7, 10.0 Hz, H-5), 2.30 (s, S-Ac), 1.52, 1.46, 1.34 and 1.32 ($CH_3$ of isopropylidene groups), 1.41 (d, J=6.8 Hz, H-7). $^{13}C$ NMR ($CDCl_3$) δ: 195.6, 109.5, 108.7, 96.7, 71.0, 71.0, 70.4, 68.8, 40.8, 30.9, 25.9, 24.9, 24.5, 17.7.

A portion of the above residue 4b (2.3 g) was dissolved in dry methanol (40 ml) at 0° C. containing 30% ammonium hydroxide (2.3 mL) and dithiothreitol (1.4 g). After 16 h at 0° C., the solvent was evaporated and the residue was dissolved in $CH_2Cl_2$, dried with anhydrous $MgSO_4$, and concentrated. Purification of the product by chromatography on a column of silica gel (ethyl acetate— hexane=1:20) afforded 5b (1.8 g). $[\alpha]_D^{25}$−58.2±2°, (c 1.02, $CHCl_3$). $^1H$ NMR ($CDCl_3$) δ: 5.56 (d, J=5.1 Hz, H-1), 4.60 (dd, J=2.6, 8.1 Hz, H-3), 4.32 (dd, J=1.8, 7.3 Hz, H-4), 4.31 (dd, J=2.6, 5.1 Hz, H-2), 3.50 (dd, J=1.5, 9.2 Hz, H-5), 3.27 (m, H-6), 2.24–2.26 (m, SH), 1.56, 1.44, 1.34 and 1.33 (H-7 and isopropylidene methyls). $^{13}C$ NMR ($CDCl_3$) δ: 109.3, 108.8, 96.6, 74.1, 70.9, 70.7, 70.53, 70.52, 35.1, 26.0, 25.9, 25.0, 24.4, 18.7.

To a solution of 5b (1.8 g) in DMF (50 ml) at −20° C., sodium hydride (134 mg) was added. After 10 min, a solution of 12a (2.8 g) in DMF (5 mL) was added and the solution was stirred at −20° C. for 16 hr. The solvent was evaporated and the residue was dissolved in $CH_2Cl_2$, washed with water, ice cold HCl (1 M) and saturated sodium bicarbonate solution, dried over anhydrous $MgSO_4$ and evaporated. Purification by chromatography on a column of silica gel (ethyl acetate— hexane-ethanol 10:10:1) gave a homogeneous product (3.5 g). $^1H$ NMR showed it to be the desired product 20b contaminated with about 10% of 13. Pure 20b was made from this mixture by removal of the acetate groups with sodium methoxide in methanol, followed by gel permeation chromatography (see below) followed by re-acetylation of the product with pyridine-acetic anhydride. $[\alpha]_D^{25}$ −38.3±2°, (c 0.98, $CHCl_3$). $^1H$ NMR ($CDCl_3$) δ: 5.56 (d, J=5.1, H-1), 5.37 (m, H-8'), 5.31 (dd, J=2.1, 7.3 Hz, H-7'), 5.12 (d, J=10.0 Hz, NH), 4.85 (m, H-4'), 4.59 (dd, J=2.4, 7.9, H-3), 4.35–4.28 (m, H-4, H-2 and H-9'a), 4.19 (dd, J=7.2, 12.6 Hz, H-9'b), 4.02 (m, H-5'), 3.91 (dd, J=2.0, 10.7 Hz, H-6'), 3.79 (s, $COOCH_3$), 3.54 (dd, J=1.7, 8.6 Hz, H-5), 3.50 (m, H-7), 2.72 (dd, J=4.6, 13.1 Hz, H-3'eq), 2.21 (dd, J=12.0, 12.9 Hz, H-3'ax), 2.14, 2.11, 2.04, 2.02 and 1.87 (5× $CH_3CO$), 1.37 (d, J=6.8 Hz, H-7), 1.51, 1.48, 1.33 and 1.31 (isopropylidene methyls). $^{13}C$ NMR ($CDCl_3$) δ: 171.0, 170.7, 170.1, 170.0, 169.97, 169.3, 109.4, 108.5, 96.7, 83.7, 74.3, 71.4, 71.1, 70.4, 69.9, 69.6, 69.4, 67.7, 62.0, 53.0, 49,5, 39.6, 38.4, 26.0, 25.98, 24.9, 24.5, 23.2, 21.1, 20.9, 20.8, 20.7, 19.7.

A portion of 20b (1.0 g) was de-O-acetylated with 0.5 M sodium methoxide (0.3 mL) in methanol (20 mL, 16 hr) and the product from this was purified by chromatography on Bio Gel P2 (200–400 mesh) to obtain pure 21b (590 mg). The isopropylidene group was removed with 50% aqueous trifluoroacetic acid (30 mL, room temperature for 4 hr), followed by filtration on a column of Bio gel P2. Finally, the methylester was converted to the sodium salt 22b with Chelex resin (Na form, 3.0 g suspended in 20 mL of water, 6 days), and this was followed by purification on a column of Bio gel P2 eluted and equilibrated with deionized water. The product fractions (as evidenced by UV absorption at 214 nm), were pooled and lyophilized to get a colorless material (400 mg). The structure was confirmed on the basis of its $^1H$ and $^{13}C$ NMR data (Tables 1 and 2). Anal. Calcd for $C_{18}H_{30}O_{13}SNa.2H_2O$: C, 38.64; H, 6.08; N, 2.50. Found: C, 39.23; H, 6.19; N, 2.70.

EXAMPLE 11

Preparation of $^{14}C$-labelled αDNeuAc (2-6)βDGal (1-4)DGlc (25)

The compound was made as described by Unversagt, C. et al., J. C., *J. Am. Chem. Soc.* 1990, 112, 9308–9309. $^{14}C$-Labeled N-acetyl-D-glucosamine ($^{14}C$-D-GlcNAc, 50 uCi, NEN, MA) was mixed with D-GlcNAc (13.5 mg, 61.1 mmole) and UDP-galactose (45.3 mg, 80 mmole), dissolved in a buffer (1.7 mL, pH 7.4) containing $MnCl_2$ (10 mmole), sodium cacodylate (50 mmole) and galactosyl transferase (5 U, EC. 2. 4. 1. 22, Sigma Chemical Company, St. Louis, Mo.), and incubated at 37° C. for 24 h. The reaction mixture was passed through a Dowex phosphate resin column (200–400 mesh) containing Chelex resin (500 mg) packed on the top. The column was eluted with deionized water (30 mL) and the eluant was concentrated to a dry residue, which was dissolved in 100 mM sodium cacodylate buffer (2.5 mL, pH 6.5) containing CMP-NeuAc (50 mg, Sigma Chemical Co.), bovine alkaline phosphatase (6 U), bovine serum albumin (5 mg) and Galβ1, 4GlcNAc a 2,6 sialyl transferase (500 mU, E. C. 2.4. 99. 5), and incubated at 37° C. for 24 hr. The reaction mixture was diluted with water to 12 mL and applied to a column of Dowex-phosphate resin (200–400 mesh) and eluted with water (75 mL). The elution buffer was then changed to 5 mM sodium phosphate buffer (pH 6.8) and fractions (7.5 mL) were collected. A sample of the fraction (10 μL) was diluted with scintillation liquid (3 mL, Formula 989, NEN, MA) and the radioactivity was measured. The products appeared in fractions 17–30. These were pooled and evaporated to a dry residue, redissolved in water and applied to a column of Sephadex G-15 (75 mL), equilibrated and eluted with deionized water. The fractions (2 mL) containing the radioactivity were pooled and lyophilized to obtain a colorless material (38 mg).

EXAMPLE 12

Hydrolysis of sialidase substrates as determined by colorimetric neuraminidase Assays The activity of neuraminidase was measured either colorimetrically in the case of the oxygen analogues or with a radiolabled substrate as in the case of the sulfur analogues.

For the colorimetric assay 10 or 20 mM stock Solutions of 16a, 16b, 19a, 19b, 22a, 22b, 23a, 23b, 23c and 25 were made and the molarity was determined based on the sialic acid content estimated by the periodate-resorcinol method (Jourdian, G. W.; et al., *S. J. Biol. Chem.* 1971, 246, 430–435). The Arthrobacter ureafacien neuraminidase (EC 3.2.1.18, specific activity 81.6 U/mg), *Clostridium perfringens neuraminidase* (EC 3.2.1.18) and *Vibrio cholerae neuraminidase* (EC 3.2.1.18) were purchased from Calbiochem® (La Jolla, Calif.). Influenza A virus (WSN H1N1) was provided by Dr. E. Cheng of DuPont-Merck Pharmaceutical, Wilmington, Dela. The virus (5.3 mg total protein content) was suspended in 50 mM sodium phosphate buffer (1 mL, pH 7.0) and thoroughly mixed and stored at −80° C. as 100 μL aliquots. Prior to use, the suspension was warmed up to 37° C. and thoroughly mixed. The following buffers were used in the enzymatic sialoside hydrolysis. For *Arthrobacter ureafaciens neuraminidase,* the buffer was 0.075 M sodium acetate—0.013 M calcium chloride at pH 5.0; for *Clostridium perfringens neuraminidase,* the buffer was 50 mM sodium acetate at pH 4.5; for *Vibrio cholerae neuraminidase,* the buffer was 50 mM sodium acetate—10 mM calcium chloride—50 mM sodium chloride (pH 5.5) and for influenza neuraminidase, the buffer was 100 mM sodium acetate (pH 5.5). The time course of neuraminidase hydrolysis (FIGS. 1 and 2) was done by incubating a 0.75 mM solution of the sialoside (in 500 μL total reaction volume, except for influenza neuraminidase reaction, where the substrate concentration was about 1 mM and the total reaction volume was 165 μL) with the neuraminidase (A. U. neuraminidase 10 mU; C. P. and V. C. neuraminidase 100 mU; influenza neuraminidase 30 μL of virus suspension) at 37° C. Samples (50 μL, except in the case of influenza neuraminidase assay, where 25 μL of sample was used) were withdrawn at 0, 15, 30, 60 and 120 min and the free sialic acid liberated was estimated by the thiobarbituric acid method as follows. The sample was diluted to 100 μL with deionized water, followed by the addition of 0.2 M sodium periodate in 9 M phosphoric acid solution (50 μL). After 20 min at room temperature, the excess periodate was destroyed with 10% sodium arsenite in 0.5 M sodium sulfate—0.1 N sulfuric acid solution (250 μL), followed by the addition of 0.6% thiobarbituric acid in 0.5 M sodium sulfate solution (1.5 mL). This mixture was kept in boiling water bath for 15 min. The samples were then cooled to room temperature, the color was extracted with cyclohexanone (2 mL) and the optical density was measured at 550 nm. To determine the Michaleis Constant ($K_m$) and $V_{max}$ (Table 3), the solutions of the sialoside substrates at six different concentrations (0.1–12.8 mM) were incubated at 37° C. for 20 min with neuraminidase in a total volume of 100 μl of the buffers (60 mL for influenza neuraminidase reaction) for 20 min. The amounts of the neuraminidase used for various sialosides are as follows: For sialoside 16a, 2 mU of A. U. neuraminidase or 25 mU of C. P. neuraminidase or 50 mU of V. C. neuraminidase, or 12 μL of the influenza virus suspension were used, for 16b, 50 mU of A. U. neuraminidase or 165 mU of C. P. neuraminidase or 50 mU of V. C. neuraminidase were used and for 23a and 23b, 2 mU of A. U. neuraminidase or 12 mU of C. P. neuraminidase or 50 mU of V. C. neuraminidase or 12 of the influenza virus suspension were used. Following incubation, a portion of the reaction mixture (50 μL) was assayed for free sialic acid content by the thiobarbituric acid method described above. As controls, the reaction was also carried out at these substrate concentrations without the neuraminidase and a correction was made for the sialic acid liberated nonenzymatically. The $K_m$ (expressed in mM) and $V_{max}$ (O. D. unit/mU of enzyme/20 min) values were determined from Lineweaver-Burk double reciprocal plots using linear fits of the data points.

TABLE 3

The Michaelis Constant ($K_m$ in mM) and $V_{max}$ (O.D./mU) of αDNeuAc(2-6)βDGal derivative 23a,isopropylidenated derivative 23b and the tg (16a) and gt (16b) rotamer analogs with neuraminidase from Influenza A virus, *Arthrobacter ureafaciens, Clostridium perfringens* and *Vibro cholerae*

| Sialo- | Influenza A | | *A. ureafaciens* | | *C. perfringens* | | *V. cholerae* | |
|---|---|---|---|---|---|---|---|---|
| side | $K_m$ | $V_{max}$ | $K_m$ | $V_{max}$ | $K_m$ | $V_{max}$ | $K_m$ | $V_{max}$ |
| 23a | 1.0 | 1.0 | 1.1 | 0.7 | 0.65 | 0.88 | 2.0 | 2.2 |
| 23b | — | — | 0.50 | 0.73 | 1.44 | 1.70 | 3.18 | 4.5 |
| 16a | 2.3 | 0.84 | 0.94 | 0.91 | 2.15 | 0.90 | 4.50 | 1.42 |
| 16b | — | — | 3.0 | 0.05 | 3.2 | 0.22 | 4.8 | 0.37 |

FIG. 1 compares the rate of hydrolysis of 0.75 mM solutions of 16a, 16b and the parent sialoside 23a by the A. U. (FIG. A), C. P. (FIG. B), V. C. (FIG. C), and influenza A (pane 1 D ) neuraminidases. A.U. Neuraminidase efficiently hydrolyzed the natural (23a) and the tg sialoside (16a) equally well, whereas there was little hydrolysis of the gt sialoside (16b) under the same experimental conditions. The C. P. neuraminidase hydrolyzed 23a faster than the tg sialoside 16a. Here again, the gt sialoside 16b was hydrolyzed very slowly. In the case of V. C. neuraminidase, the natural sialoside 23a was the most preferred substrate of the three sialosides. Comparison between the tg 16a and gt sialoside 16b indicated that 16a was preferentially hydrolyzed. Influenza A neuraminidase hydrolyzed both the natural sialoside 23a and the tg sialoside 16a (about two fold slower than 23a), whereas the gt sialoside was not hydrolyzed at all. Thus, all four neuraminidases hydrolyze the tg sialoside 16a preferentially, as compared to 16b, even though the selectivity between 16a and 16b appeared to be dependent on the source of the neuraminidase.

The hydrolysis of sialosides 16a, 16b, 23a was carried out at various substrate concentrations in order to determine detailed enzyme kinetic parameters. Control reactions were carried out at all substrate concentrations without the enzyme and a correction for the nonenzymic hydrolysis was done. The hydrolysis profile in FIG. 2 shows the difference in enzymatic hydrolysis behavior of the two analogs 16a and 16b. From the Lineweaver-Burk plots, the Michaelis constant $K_m$ and the maximum rate of enzyme hydrolysis $V_{max}$ for these three substrates 16a, 16b and 23a were calculated and these results are presented in Table 3.

As can be seen from FIG. 2, the neuraminidase cleavage of sialic acid was facile for the tg sialoside 16a but was very slow for 16b. Since no significant amount of hydrolysis took place for gt sialoside 16b under the conditions used for 16a, a 10 to 20 fold higher concentration of the enzymes (A. U., C. P. and V. C., see Experimental) relative to that used for 16a was used to determine $K_m$ and $V_{max}$. Due to the limited solubility of the influenza virus, a higher concentration of viral suspension could not be prepared to effect measurable hydrolysis of gt sialoside 16b and therefore the $K_m$ and $V_{max}$ could not be determined.

Table 3 shows that with influenza virus, C. P. and V. C. neuraminidases, the $K_m$ for 16a was 2 to 3 fold higher than for the natural sialoside 23a, whereas the $V_{max}$ was nearly the same. However, with the A. U. neuraminidase, these two substrates behaved nearly identically. On the other hand, the $K_m$ for the gt sialoside 16b was generally higher than that of either 16a or 23a. Most notably, the $V_{max}$ was substantially smaller (4 to 18 fold lower than 16a or 23a).

In order to elucidate whether the galactose hydroxyl groups or the sialoside aglycon itself has any role in the enzymatic reactions, the hydrolysis of the isopropylidene analogs of the natural sialoside 23a and the two analogs 16a and 16b were carried out (compounds 23b, 19a and 19b, respectively). It is to be noted that the isopropylidenation in these derivatives not only masks the galactose hydroxyls, but also changes the pyranose ring chair conformation into a boat structure As shown in FIG. 3 (FIG. A–D), the isopropylidene derivative of the natural sialoside 23b was in fact more efficiently hydrolyzed by all four neuraminidases. The $K_m$ for 23b was lower compared to 23a with A. U. neuraminidase (Table 3), and higher with C. P. and V. C. neuraminidases. The lower affinity of 23b for these latter two enzymes was compensated by higher $V_{max}$ as compared to 23a. The isopropylidenation of the tg sialoside as seen in 19a had no effect on the hydrolysis with A. U. and V. C. neuraminidase (FIG. 3, panels A and C) as compared to 16a, but had a detrimental effect with the C. P. and influenza A neuraminidase (FIG. 3, panels B and D). The isopropylidene derivative 19b of the gt sialoside was inactive with all the four enzymes and, in fact, was more resistant to enzymatic hydrolysis as compared to 16b (compare FIGS. 2 and 3). Based on this, it was concluded that the substitution at galactose hydroxyls has a marginal effect only on the enzymatic hydrolysis of sialic acid.

EXAMPLE 13

Inhibition of hydrolysis of sialidase substrates by thiosialosides as determined by radiolabeled neuraminidase Assays For the radiolabled assay the inhibition constants (Ki) for 22a and 22b were determined by incubating (37° C.) a solution of 25 at four different concentrations (approximately at 0.5, 1, 2 and 4 times the Km of 25 for the enzyme), with the neuraminidase, in the presence (at three inhibitor concentrations) or absence of the inhibitors, for 20 or 30 min. This was followed by estimating the amount of free LacNAc liberated. The buffers used in these neuraminidase reactions were the same as described above. The four concentrations of 25 used in these neuraminidase assays were: A.U. neuraminidase, 0.5, 1.0, 2.0 and 4.0 mM; influenza A neuraminidase, 1.0, 2.0, 4.0 and 8.0 mM; C. P. neuraminidase, 0.5, 1.0, 2.0 and 4.0 mM; V. C. neuraminidase 4.0, 6.0, 8.0 and 10 mM. The inhibitor concentrations were: 22a, 0.5, 1.0 and 2.0 mM for A. U. and C. P. neuraminidases; 0.6, 1.2 and 2.4 mM for influenza A neuraminidase; 1.0, 2.0 and 2.9 mM for V. C. neuraminidase: 22b, 2.5, 5.0 and 10 mM for influenza A neuraminidase; 0.95, 1.90 and 3.8 mM for C. P. neurarninidase and 1.9, 3.8 and 5.5 mM for A. U. and V. C. neuraminidases. The neurarninidase concentrations were: 2 mU of A. U. neuraminidase in 100 ul of total reaction mixture; 53 ug of influenza A virus in 50 ul of total reaction volume; 12.5 mU of C. P. neuraminidase in 50 ul total reaction volume; and 12.5 mU of V. C. neuraminidase in 25 ul of total reaction volume. After the reaction, the reaction mixture was diluted with deionized water (1 mL), and passed through a column of Dowex resin (phosphate form, 200–400 mesh, 2 mL of a 1 g/mL suspension of the resin in deionized water). The column was further eluted with deionized water (2 mL). Under these conditions, only the free LacNAc eluted. The eluant was diluted with Scintillation fluid (10 mL, Formula 989, NEN, MA) and the radioactivity was measured for 5 min with a Liquid Scintillation Counter. From the Dixon plots for the hydrolysis of 25 the inhibition constant Ki was calculated according to methods well known in the art.

Figure 4A:
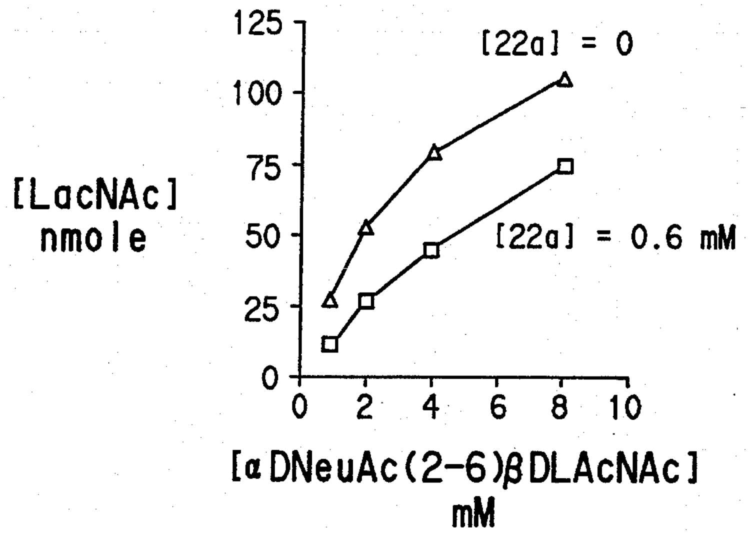
FIG. 4 illustrates the hydrolysis of the radiolabled susbstrate 25 by influenza A neuraminidase in the absence (indicated by Δ) and the presence of (indicated by Δ) thiosialoside inhibitors 23c, 22a, and 22b.
Figure 4B:
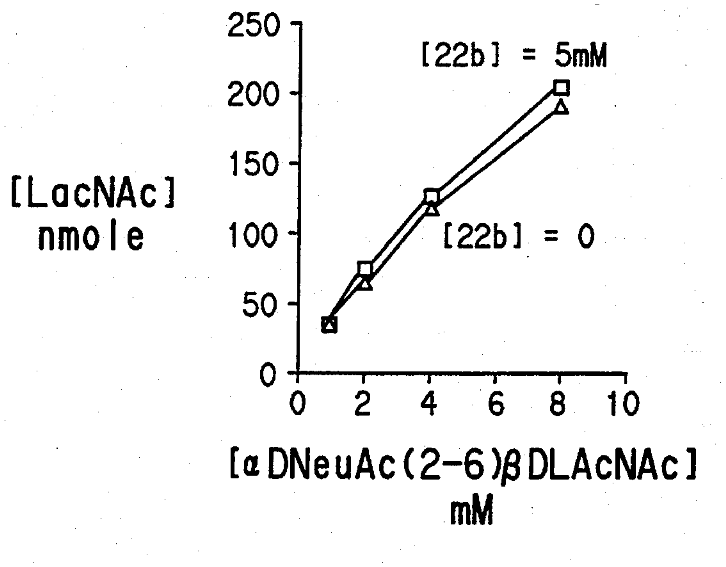
Figure 4C:
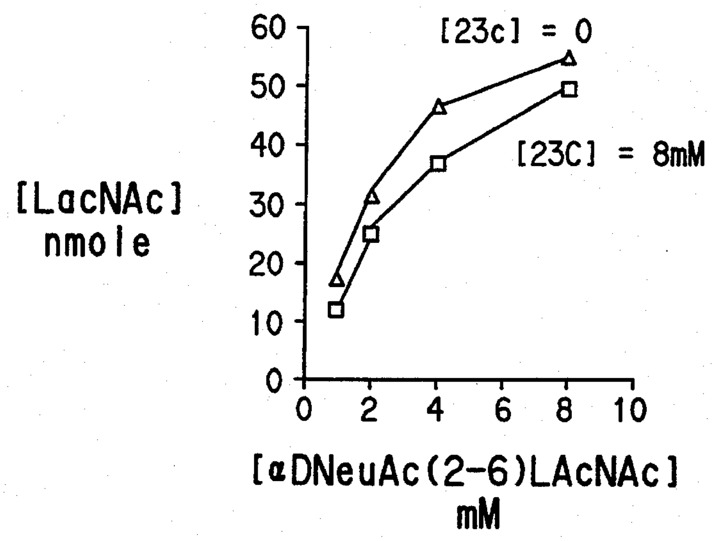
Figure 5A:
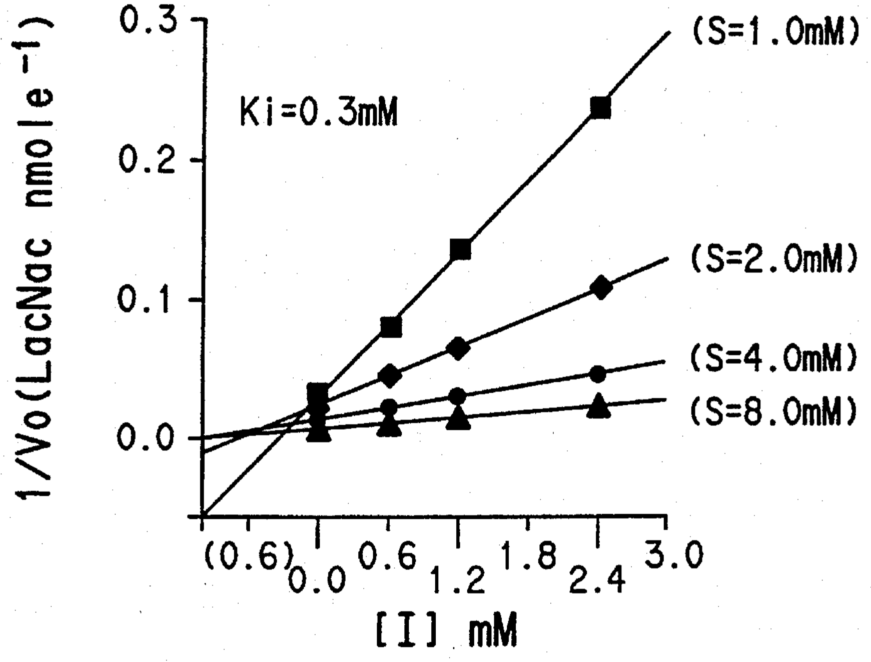
FIG. 5 are Dixon plots of the inhibition by 22a (indicated by "I") for the hydrolysis of radiolabled 25 (indicated by "S") by neuraminidases from influenza A (FIG. 5A), *A. ureafaciens* (FIG. 5B), *C. perfringens* (FIG. 5C), and *V. cholerae* (FIG. 5D).
Figure 5B:
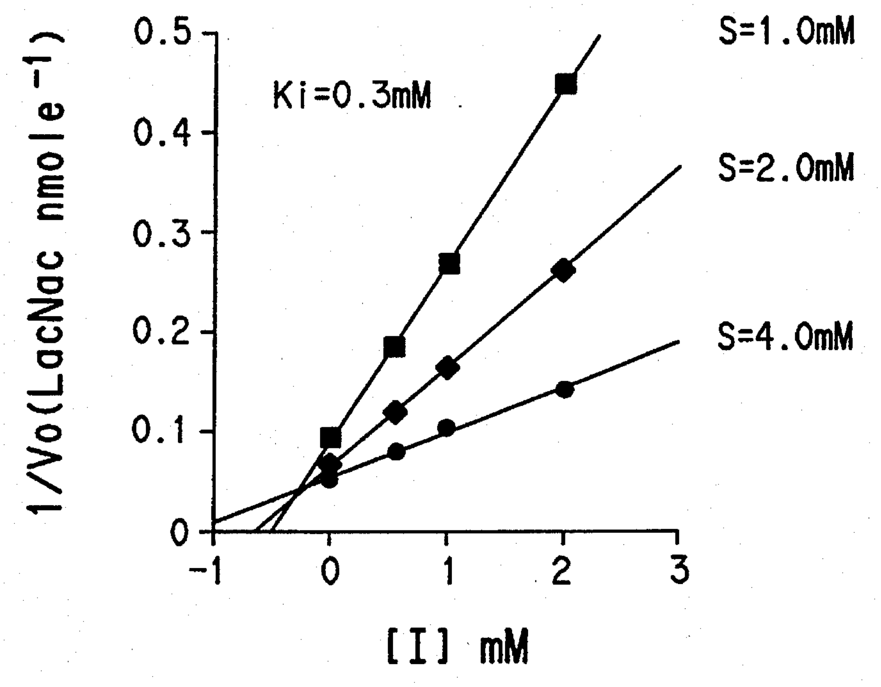
Figure 5C:
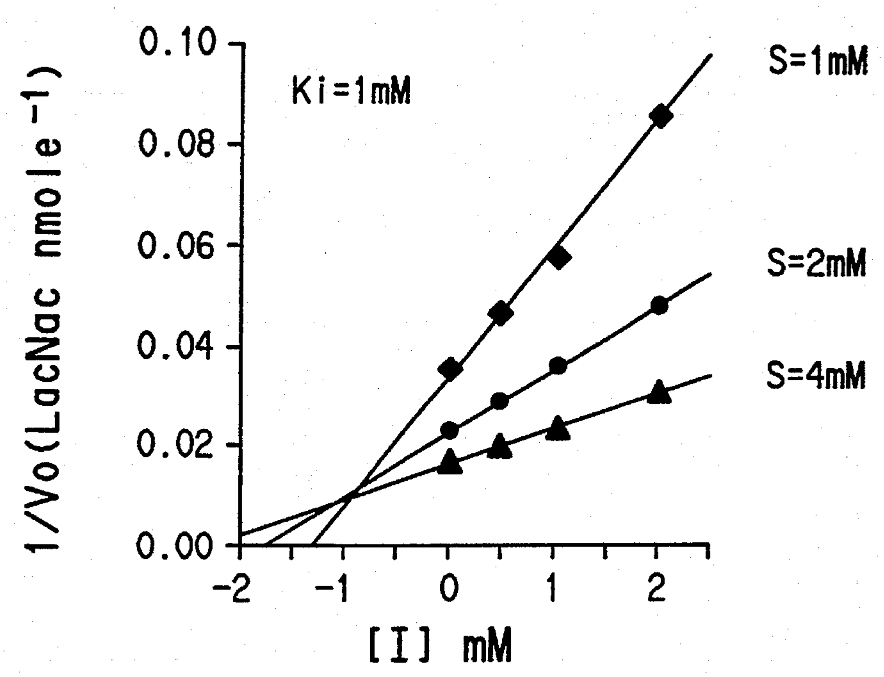
Figure 5D:
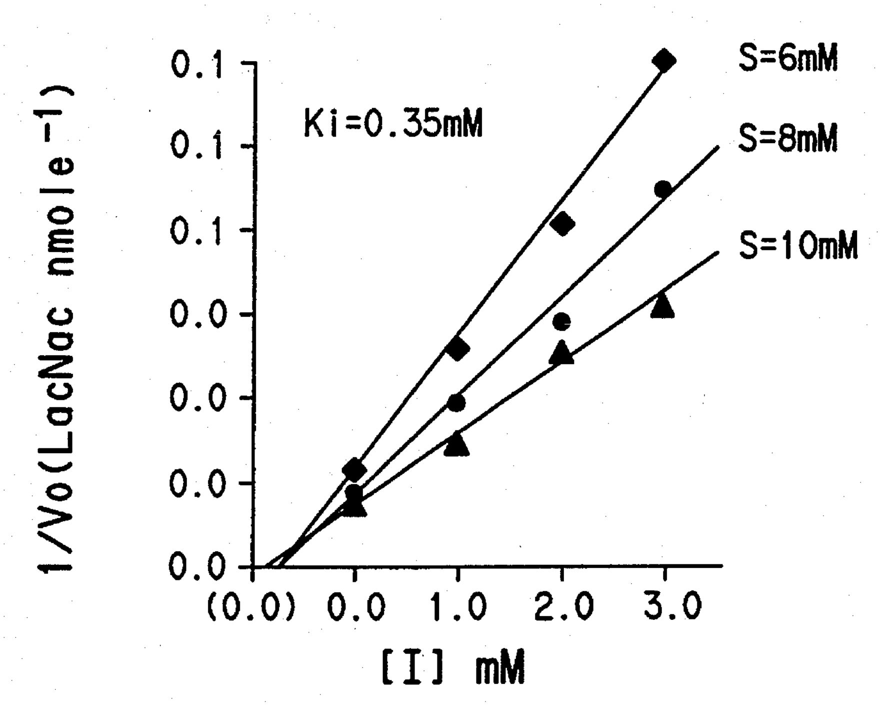
Figure 6A:
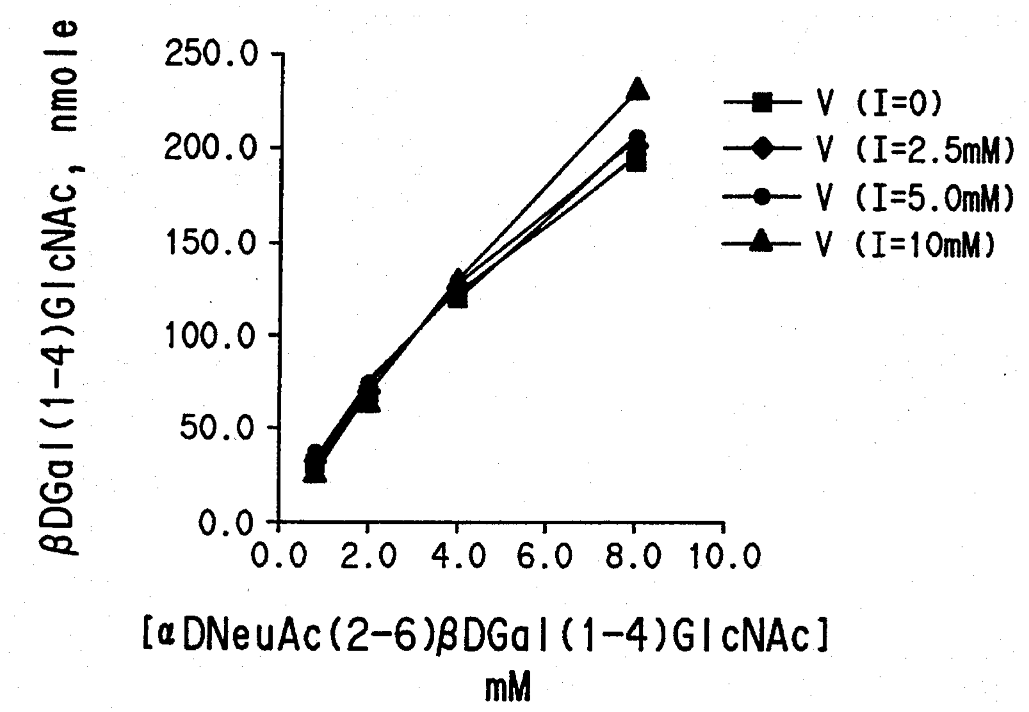
FIG. 6 illustrates the lack of inhibition by 22b for the hydrolysis of radiolabled 25 by neuraminidases from influenza A (FIG. 6A), *A. ureafaciens* (FIG. 6B), *C. perfringens* (FIG. 6C), and *V. cholerae* (FIG. 6D) .
Figure 6B:
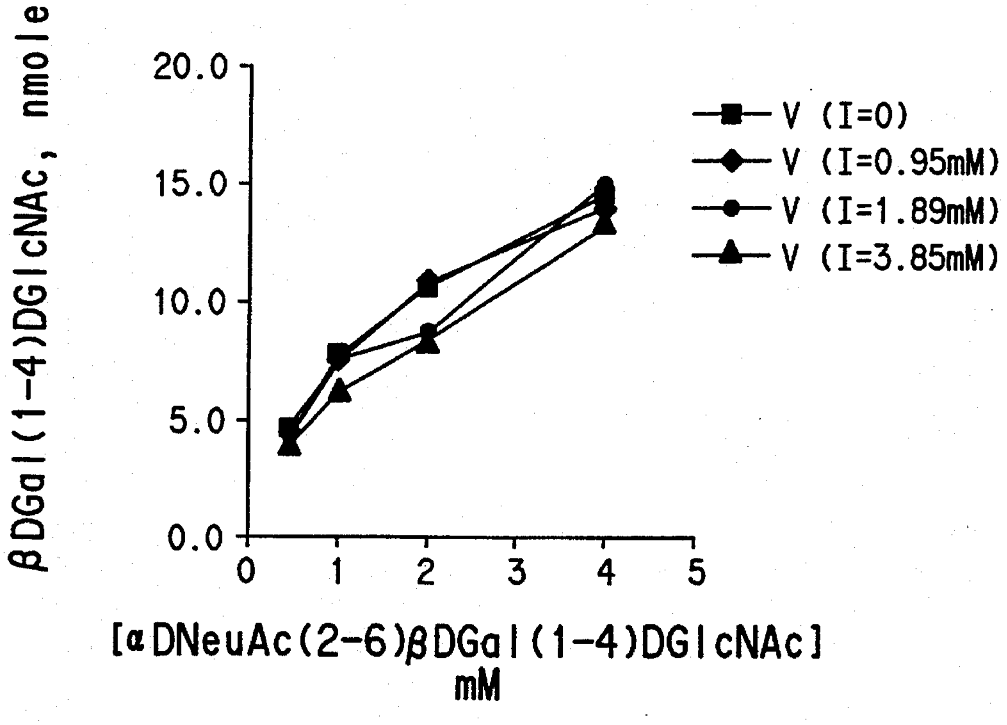
Figure 6C:
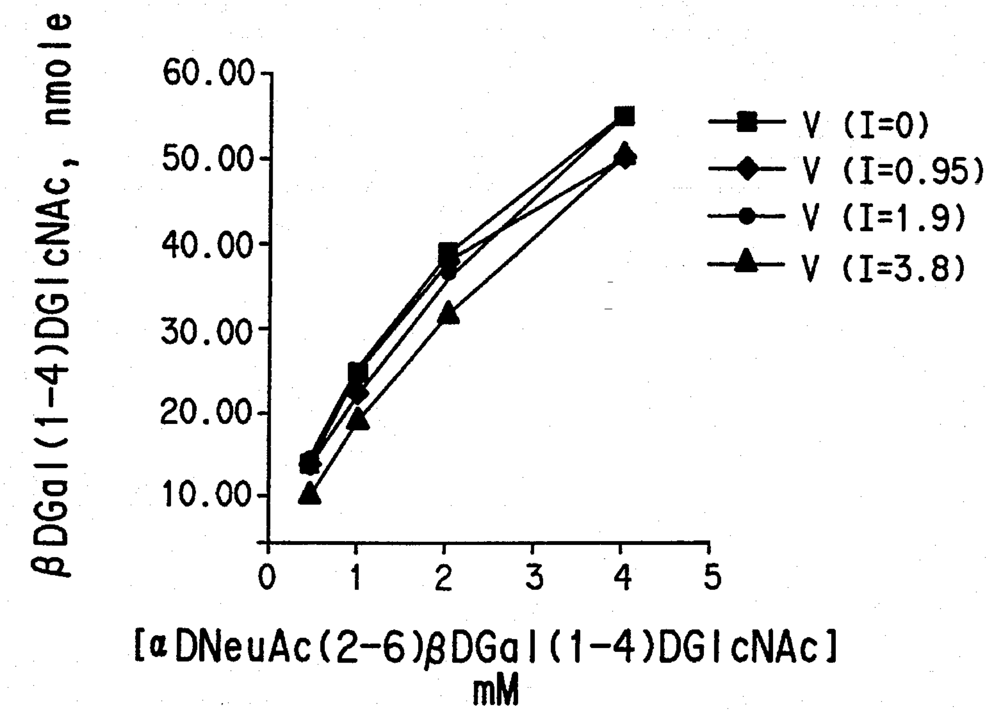
Figure 6D:
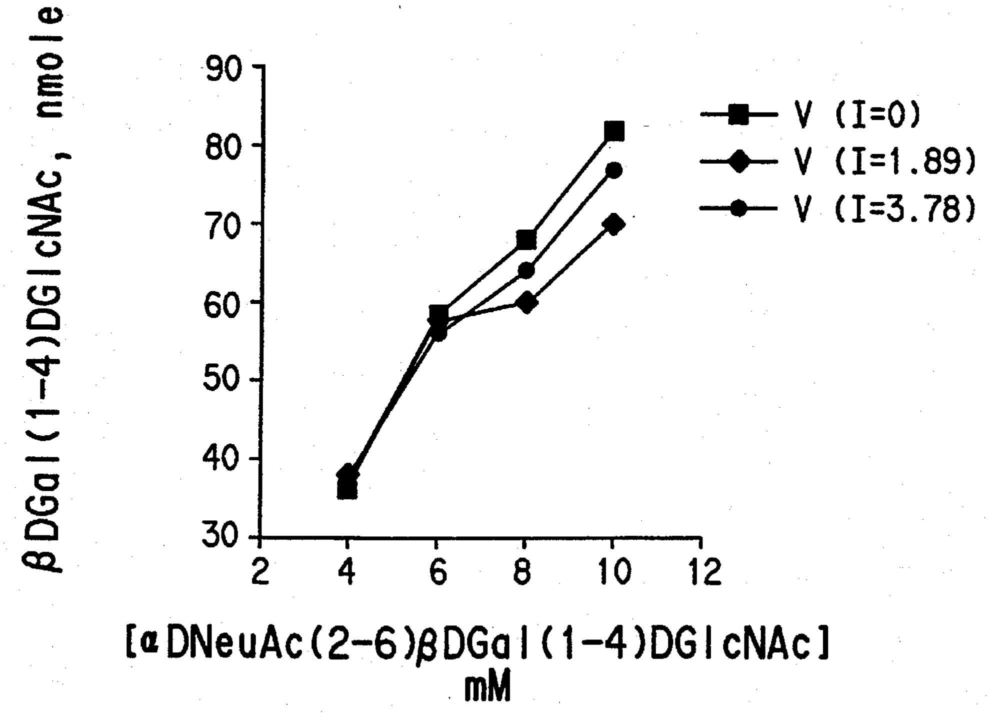

FIG. 4, panel A shows the influenza virus neuraminidase hydrolysis of 25 in the absence (I=0) and in the presence of 22a (I=0.6 mM), panel B for 22b (I=0 and 5 mM) and panel C for 23c (I=0 and 8 mM). It is evident from these results, that only the tg thiosialoside analog 22a was a good inhibitor (Ki=0.3 mM) of influenza neuraminidase. Similar experiments with A. U., C. P. and V. C. neuraminidases showed that only 22a was a good inhibitor (Ki for 22a with A. U., C. P. and V. C. are 0.3, 1.0 and 0.35 mM, respectively; see FIG. 5). The gt analog 22b showed very little inhibition at 5 mM or higher concentrations (FIG. 6). Similarly, 23c exhibited only weak inhibition when examined with A. U. neuraminidase. Thus, there was a parallel in the behavior of oxygen and the sulfur analogs of tg (16a and 22a) and gt (16b and 22b) sialosides, which was not the case with the natural sialoside 23a and its thio analog 22c.

What is claimed is:

1. A method for inhibiting sialidase activity comprising contacting sialidase with a compound of Formula I

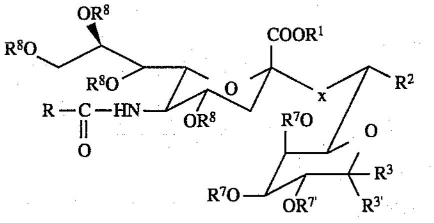

I wherein

R is H or $C_1$ to $C_{20}$ hydrocarbyl or substituted hydrocarbyl;

$R^1$ is H, a $C_1$ to $C_{20}$ alkyl, a mono, di or polyvalent cation of an alkali metal, alkaline earth metal or transition metal, or an ammonium or substituted ammonium ion;

X is O, S, $CR^4R^5$ or $NR^6$, wherein $R^4$, $R^5$, $R^6$ are each independently H or a $C_1$ to $C_{20}$ hydrocarbyl or substituted hydrocarbyl;

$R^2$ is a $C_1$ to $C_{20}$ hydrocarbyl or substituted hydrocarbyl;

$R^3$ and $R^{3'}$ are H, OH, a $C_1$ to $C_{20}$ alkoxy or substituted alkoxy, a mono, di or oligosaccharide, or a $C_1$ to $C_{20}$ alkylideneoxy taken together with $R^{7'}$ when $R^{7'}$ is not H; provided that one of $R^3$ or $R^{3'}$ must be H but $R^3$ and $R^{3'}$ may not both be H;

$R^7$ and $R^{7'}$ are independently H, a $C_1$ to $C_{20}$ acyl, a $C_1$ to $C_{20}$ alkyl, or a $C_1$ to $C_{20}$ alkylidene taken together with an adjacent $R^{3'}$, $R^7$ or R7'; and $R^8$ is H, a $C_1$ to $C_{20}$ acyl, or a $C_1$ to $C_{20}$ alkyl.

2. The process of claim 1 wherein in formula I R is methyl;

$R^1$ is Na or $CH_3$;

$R^2$ i s $CH_3$;

$R^8$ is H or acetyl;

$R^7$ is H or alkylidene taken together with $R^{3'}$;

$R^{7'}$ is acetyl or benzyl;

$R^3$ is OH when $R^{3'}$ is H;

$R^{3'}$ is OH when $R^3$ is H; and

X is S.

* * * * *